(12) United States Patent
Kilck et al.

(10) Patent No.: US 8,367,639 B2
(45) Date of Patent: *Feb. 5, 2013

(54) HYDROGELS WITH COVALENT AND NONCOVALENT CROSSLINKS

(75) Inventors: Kristi L. Kilck, Rising Sun, MD (US); Nori Yamaguchi, Newburgh, IN (US)

(73) Assignee: University of Delaware, Newark, DE (US)

( * ) Notice: Subject to any disclaimer, the term of this patent is extended or adjusted under 35 U.S.C. 154(b) by 88 days.

This patent is subject to a terminal disclaimer.

(21) Appl. No.: 12/814,826

(22) Filed: Jun. 14, 2010

(65) Prior Publication Data

US 2011/0033543 A1 Feb. 10, 2011

Related U.S. Application Data

(63) Continuation-in-part of application No. 12/767,931, filed on Apr. 27, 2010, and a continuation-in-part of application No. 11/395,902, filed on Mar. 31, 2006, now Pat. No. 7,737,131.

(60) Provisional application No. 60/666,787, filed on Mar. 31, 2005.

(51) Int. Cl.
*A61K 31/727* (2006.01)
*A61K 31/715* (2006.01)
*A61K 38/00* (2006.01)
*C08B 37/10* (2006.01)

(52) U.S. Cl. ............ 514/56; 514/54; 514/23; 536/21; 424/488; 424/486

(58) Field of Classification Search .............. 514/56, 514/54, 23, 2; 536/21; 424/488, 486
See application file for complete search history.

(56) References Cited

U.S. PATENT DOCUMENTS

| | | | |
|---|---|---|---|
| 4,323,525 | A | 4/1982 | Bornat |
| 4,689,525 | A | 8/1987 | Shimoma et al. |
| 2001/0045547 | A1 | 11/2001 | Senecal et al. |
| 2002/0084178 | A1 | 7/2002 | Dubson et al. |
| 2002/0100725 | A1 | 8/2002 | Lee et al. |
| 2002/0175449 | A1 | 11/2002 | Chu et al. |
| 2003/0106294 | A1 | 6/2003 | Chung et al. |
| 2003/0137069 | A1 | 7/2003 | Reneker |
| 2003/0168756 | A1 | 9/2003 | Balkus, Jr. et al. |
| 2003/0195611 | A1 | 10/2003 | Greenhalgh et al. |
| 2003/0215624 | A1 | 11/2003 | Layman et al. |
| 2004/0013873 | A1 | 1/2004 | Wendorff et al. |
| 2004/0018226 | A1 | 1/2004 | Wnek et al. |
| 2004/0037813 | A1 | 2/2004 | Simpson et al. |
| 2004/0038014 | A1 | 2/2004 | Schaefer et al. |

OTHER PUBLICATIONS

The Biomedical Engineering Handbook; "Tissue Engineering and Artificial Organs"; Taylor & Francis Group; Section 32; pp. 32-1 thru 32-22, (2006).

Bioconjugate Techniques; Academic Press; Modification of Sugars, Polysaccharides, and Glycoconjugates, pp. 27-30; Amine-Reactive and Sulfhydryl-Reactive Cross-linkers 235-239; 1996.
Yamaguchi, Nori et al., "Polysaccharide-Poly(ethylene glycol) Star Copolymer as a Scaffold for the Production of Bioactive Hydrogels"; Biomacromolecules 2005, 6, pp. 1921-1930.
Yamaguchi, Nori, et al., "Rheological Characterization of Polysaccharide-Poly(ethylene glycol) Star Copolymer Hydrogels", Biomacromolecules, 2005, 6, pp. 1931-1940.
Seal, Brandon L., et al., "Physical Polymer Matrices Based on Affinity Interactions Between Peptides and Polysaccharides", Biomacromolecules, 2003, 4, pp. 1572-1582.
Miyata, Takashi, et al., "A reversibly antigen-responsive hydrogel", Nature vol. 399, Jun. 24, 1999, pp. 766-769.
Xu, Chunyu, et al., "Reversible Hydrogels from Self-Assembling Genetically Engineered Protein Block Copolymers"; Biomacromolecules, 2005, 6, pp. 1739-1749.
Wang, Chun, et al., "Hybrid Hydrogels assembled from synthetic polymers and coiled-coil protein domains"; Nature vol. 397, Feb. 4, 1999, pp. 417-420.
Petka, Wendy A., et al., "Reversible Hydrogels from Self-Assembling Artificial Proteins", Science vol. 281, Jul. 17, 1998, pp. 389-392.
Sato, Haruya "Enzymatic procedure for site-specific pegylation of proteins", Advanced Drug Delivery Reviews, 54, 2002, pp. 487-504.
Deiters, Alexander, et al., "Site-specific PEGylation of proteins containing unnatural amino acids", Bioorganic & Medicinal Chemistry Letters, 14, 2004, pp. 5743-5745.
Shin, Heungsoo, et al., "Biomimetic materials for tissue engineering"; Biomaterials, 24, 2003, pp. 4353-4364.
Huang, Zheng-Ming, et al., "A review on polymer nanofibers by electrospinning and their applications in nanocomposites"; Composites Science and Technology, 63, 2003, pp. 2223-2253.
Jin, Hyoung-Joon, et al., "Human bone marrow stromal cell responses on electrospun silk fibroin mats"; Biomaterials, 25, 2004, pp. 1039-1047.
Jin, Hyoung-Joon, et al., "Electrospinning Bombyx mori silk with poly(ethylene oxide)"; Biomacromolecules, 2002, 3, pp. 1233-1239.
Li, Wan-Ju, et al., "Electrospun nanofibrous structure: A novel scaffold for tissue engineering"; Journal of Biomed Mater Res 60, (2002), pp. 613-621.
Sukigara, Sachiko, et al., "Regeneration of Bombyx mori silk by electrospinning—part 1: processing parameters and geometric properties"; Polymer 44, 2003, pp. 5721-5727.
Tae, Giyoong, et al., "Formation of a Novel Heparin-Based Hydrogel in the Presence of Heparin-Binding Biomolecules", Biomacromolecules, vol. 8, No. 6., (2007), pp. 1979-1986.
van de Weert, Marco, et al., "Complex Coacervation of Lysozyme and Heparin: Complex Characterization and Protein Stability", Pharmaceutical Research, vol. 21, No. 12, Dec. 2004, pp. 2354-2359.
Robinson, Christopher J., et al., "VEGF 165-binding Sites within Heparan Sulfate Encompass Two Highly Sulfated Domains and Can Be Liberated by K5 Lyase", Journal of Biological Chemistry, vol. 281, No. 3, Jan. 20, 2006, pp. 1731-1740.
Ashikari-Hada, Satoko, et al., "Characterization of Growth Factor-binding Structures in Heparin/Heparan Sulfate Using an Octasaccharide Library", The Journal of Biological Chemistry, vol. 279, No. 13, Issue of Mar. 26, 2004, pp. 12346-12354.

(Continued)

*Primary Examiner* — Shaojia Anna Jiang
*Assistant Examiner* — Michael C Henry
(74) *Attorney, Agent, or Firm* — McCarter & English

(57) ABSTRACT

A method for targeted delivery of therapeutic compounds from hydrogels is presented. The method involves administering to a cell a hydrogel in which a therapeutic compound is noncovalently bound to heparin. The hydrogel may contain covalent and non-covalent crosslinks.

12 Claims, 29 Drawing Sheets

OTHER PUBLICATIONS

Kim, Sung Hye, et al., "Cell-mediated Delivery and Targeted Erosion of Vascular Endothelial Growth Factor-Crosslinked Hydrogels", Macromolecular Rapid Communications, 31, (2010), pp. 1231-1240.

Nie, Ting, et al., "Production of heparin-functionalized hydrogels for the development of responsive and controlled growth factor delivery systems", Journal of Controlled Release, 122, (2007), pp. 287-296.

Yamaguchi, Nori, et al., "Growth Factor Mediated Assembly of Cell Receptor-Responsive Hydrogels", Journal of American Chemical Society, 129, (2007), pp. 3040-3041.

FIGURE 1
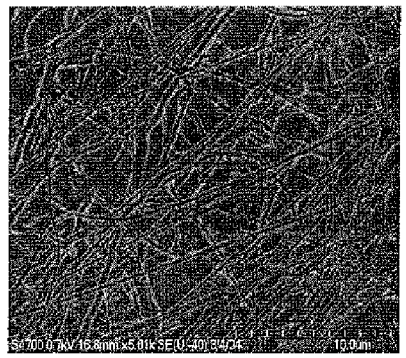
FIGURE 2
A B
 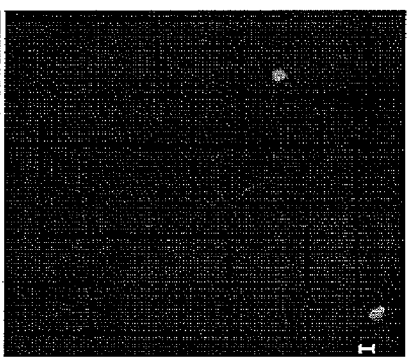

FIGURE 10
PEG-LMWH-Dye/PLGA          LMWH-Dye/PLGA
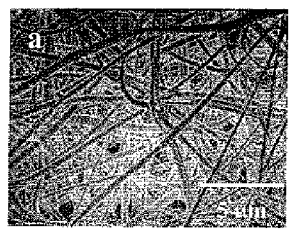 After 6 h incubation in PBS 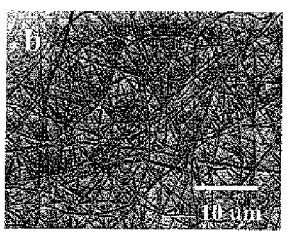
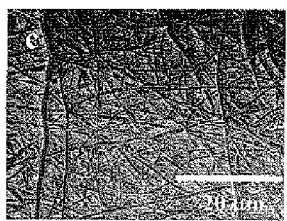 After 1 day incubation in PBS 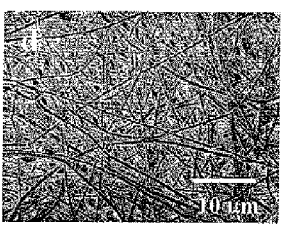
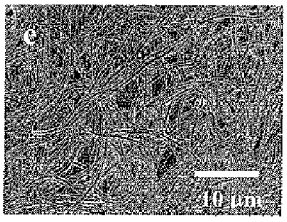 After 3 days incubation in PBS 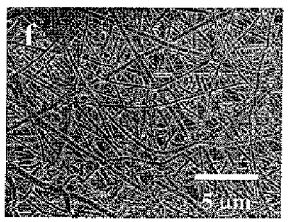
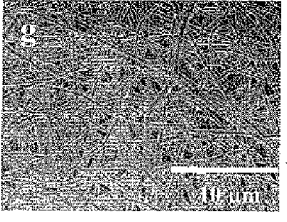 After 14 days incubation in PBS

FIGURE 11 (a-d)
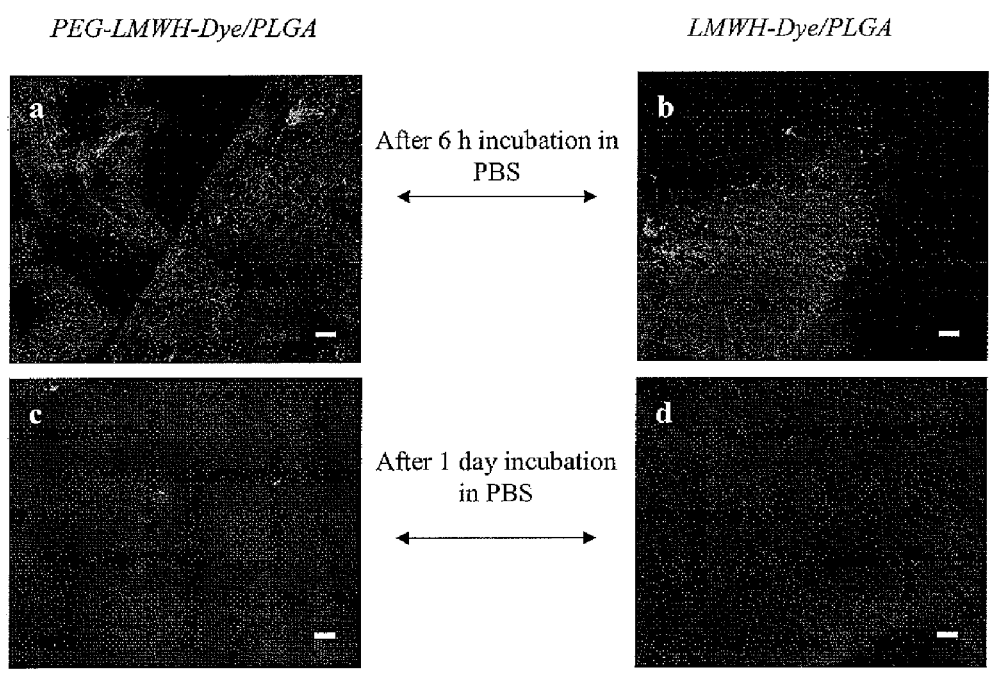

FIGURE 11 (e-h)
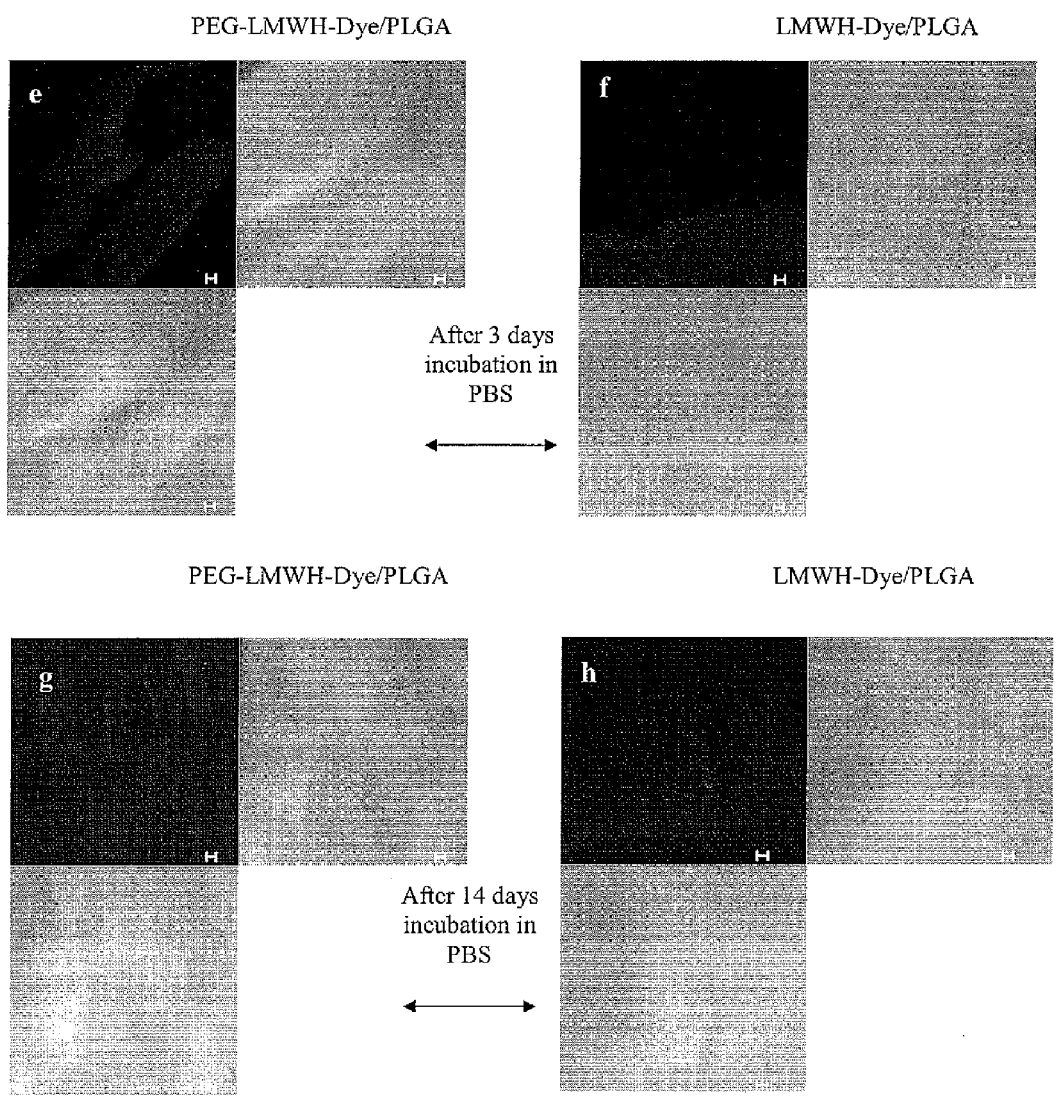

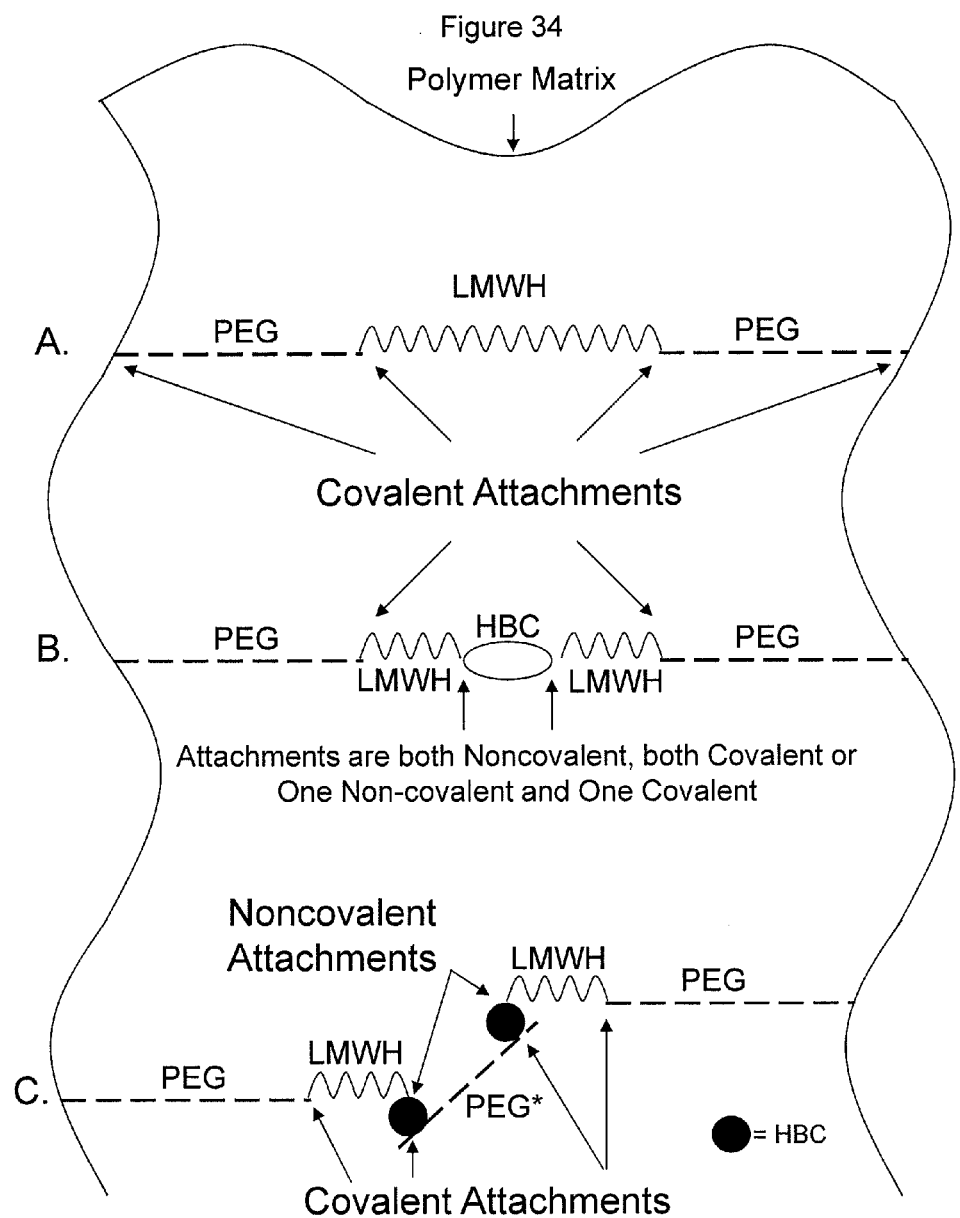

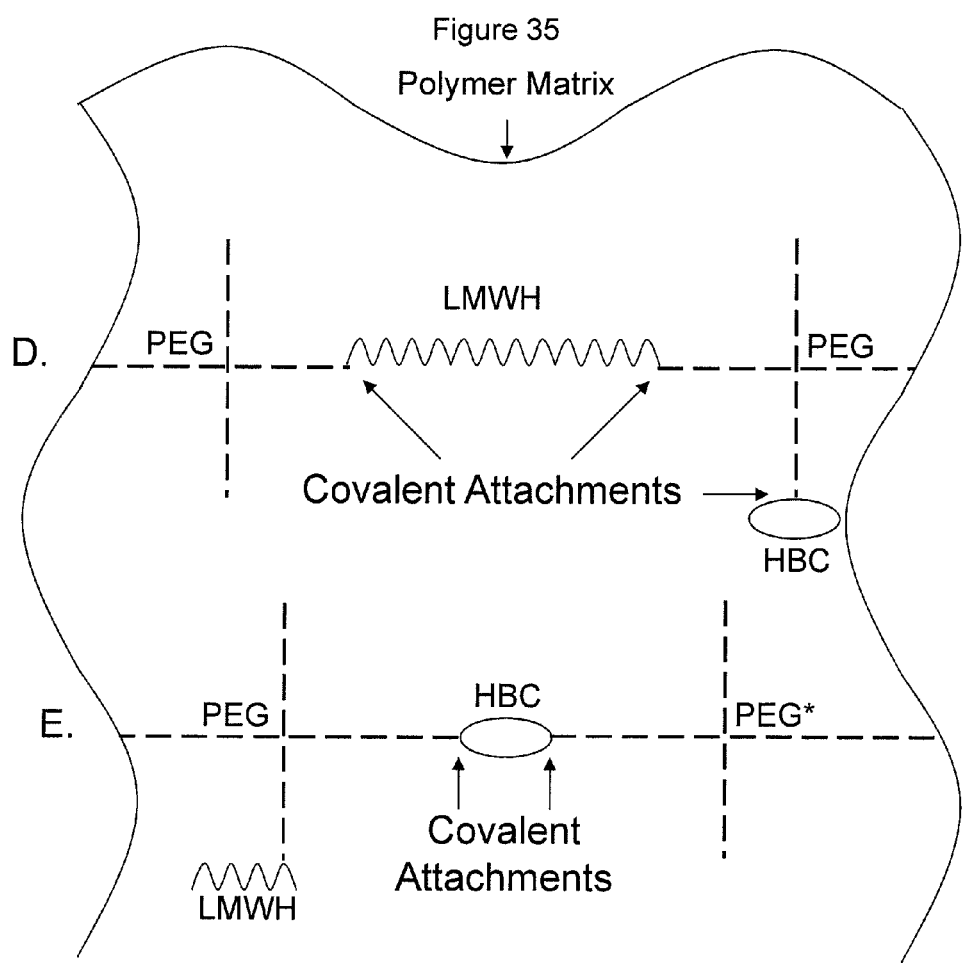

HYDROGELS WITH COVALENT AND NONCOVALENT CROSSLINKS

CROSS REFERENCE TO RELATED APPLICATIONS

This application claims the benefit of U.S. Provisional Application No. 60/666,787, filed Mar. 31, 2005, U.S. patent application Ser. No. 11/395,902, filed Mar. 31, 2006 now U.S. Pat. No. 7,737,131, of which it is a continuation-in-part, and U.S. patent application Ser. No. 12/767,931, filed Apr. 27, 2010, of which it is a continuation-in-part. The contents of each of these priority applications are incorporated herein by reference.

RELATED FEDERALLY SPONSORED RESEARCH

The work described in this application was sponsored by the following Federal Agencies: NSF NIRT under Contract Number DMR-0210223, NASA under Contract Number NAGS-01923, NIH, Nanoscale Engineering, under Contract Number ROI EB003172, and NIH under Contract Number RO1-EB006006.

FIELD OF THE INVENTION

The present invention relates generally to a hydrogels comprising covalent and noncovalent crosslinks.

BACKGROUND OF THE INVENTION

Over the past two decades the development of novel drug delivery systems has had a tremendous impact on medicine, allowing for the improvement of many existing therapeutics as well as enabling the use of entirely new therapies. Along with these improvements there has been a move to miniaturize drug delivery devices from the macroscale (>1 mm) to the microscale (100-0.01 μm) or nanoscale (100-1 nm). One goal of developing these devices is to provide for the in situ delivery of therapeutic compounds. Therefore, a main area of investigation concerns the development of integrated systems that combine the nanotechnology with therapeutic molecules, for example, drugs, or biopolymers.

However, these new technologies must overcome several crucial and significant obstacles. For example, new approaches are required that allow for the delivery of insoluble, or unstable compounds. In addition, these approaches must address situations in which the therapeutic molecule is rare, or difficult to purify. Furthermore, these approaches must allow for localized delivery of potent compounds, and provide for improved compliance by reducing the chances of missing or erring in a dose. Lastly, these devices cannot be so small that they are unable to deliver an adequate dose.

In addition, to date a number of peptides and proteins have been explored for pharmaceutical applications by virtue of their high biological activity and specificity. Despite potential advantages offered by these drugs, their application may suffer because of the high molecular weight, hydrophilicity and low stability, which are reflected in poor biopharmaceutical properties. In particular, peptides and proteins undergo rapid clearance from the body, which takes place by a combination of events including proteolysis, renal ultrafiltration, and liver clearance.

The development of functionalized polymers that can elicit specific biological responses, as well as the development of methods to fabricate these biologically functionalized polymers, is a viable approach for such therapeutic applications, in which delivery of molecules such as those above is desirable. For example, the generation of fibrous matrices with biological properties and fiber diameters commensurate with those of the natural extracellular matrix (ECM) may permit the development of novel materials for use not only in drug delivery, but also in wound healing or tissue engineering.

Synthetic polymers, which can be designed to mimic some functions of biopolymers, have been actively developed as drug delivery matrices due to their industrial and scientific value. They represent a primary polymeric vehicle for the delivery of drugs and biomolecules, owing to their simple synthesis, ease of processing, and range of physical properties. Polymers such as proteins, polysaccharides, and nucleic acids, which are present as basic components in living organic systems, have also found some use in drug delivery and biomaterials applications, particularly for biopolymers such as collagen and alginate, which have desired mechanical and biological properties. There remains a significant need, however, for the facile production of polymeric materials in which mechanical and biological properties can be easily modified in a modular fashion, without relying solely on the naturally occurring mechanical properties of the biological polymers or the lack of biological activity of synthetic polymers.

One approach to the use of polymers in drug delivery applications involves the response of a polymer system to certain stimuli, which is a common process for biopolymers in living organisms. Stimuli responsive polymers can provide a variety of applications for the biomedical fields. The interest in these polymers has increased dramatically due to their promising potential. Among others, temperature and pH responsive mechanisms have been investigated as they are relatively convenient and effective stimuli in a variety of applications. Such stimuli-responsive polymers have been utilized in various forms, including cross-linked (permanently) hydrogels, reversible hydrogels, micelles, modified interfaces, and conjugated solutions, among others.

There has also been developing interest by the scientific community in applying methods from engineering and the life sciences to create artificial constructs directed to tissue regeneration, and thus, providing a minimally invasive and less painful way to treat patients. The basic protocol for the tissue engineering approach includes isolating specific cells by obtaining them through a biopsy from a patient, growing them on a three-dimensional scaffold under controlled culture conditions, delivering the construct to the desired location in the patient's body and directing new tissue formation into the scaffold that will be degraded over time. Successful regeneration of damaged organs or tissues based on tissue engineering requires several critical elements, not the least of which includes biomaterial scaffolds that serve as a mechanical support for cell growth.

Materials are important in most tissue engineering strategies as they can serve as a substrate on which cell populations can attach and migrate, be implanted with a combination of specific cell types as a cell delivery vehicle, and be utilized as a drug carrier to activate specific cellular function in the localized region.

The modification of biomaterials with bioactive molecules has been found useful in designing biomimetic scaffolds that can provide biological cues to elicit specific cellular responses and direct new tissue formation. The surface and bulk modification of materials with peptide sequences or with bioactive proteins or other biomolecules, for example, can allow for the modulation of cellular functions such as adhesion, proliferation and migration through alterations of peptide concentration or its spatial distribution. A variety of cell binding peptides have been introduced into three dimensional networks through physical, chemical, photochemical, and ionic crosslinking. The molecules have been attached to a variety of polymeric substrates for varying applications, but a need still remains for methods for simple modification of materials with multiple bioactive molecules in a manner that can control their release.

Electrospinning is an attractive approach to polymer processing. The control of fiber diameter, porosity, and fiber surface morphology makes electrospun fibers useful in a range of applications including filtration, electronic, and biomedical applications. Electrospun fibers are ideal for use in biomedical applications such as tissue engineering and drug delivery due to the three-dimensional nanometer scale matrix that can be quickly produced using small quantities of starting material (<50 mg) on the laboratory scale. Larger matrices can also easily be made via the scaling up of materials that prove to have useful materials and biological properties on the laboratory scale. Collagen, fibrinogen, chitosan, poly(lactic acid), poly(L-lactide-co-β-caprolactone), and poly(D,L-lactide-co-glycolide) are just a few of the polymers being investigated for use in electrospun drug delivery and tissue engineering constructs due to their biocompatibility. Electrospun fibers mimic the size scale of fibrous proteins found in the extracellular matrix (50-150 nm) and the three-dimensional nature of the matrix allows for cells to infiltrate the matrix and proliferate. A variety of additional polymers can also be electrospun into matrices for drug delivery, tissue engineering, and other applications. For example, see Z. M. Huang, Y. Z. Zhang, M. K. Kotaki and S. Ramakrishna, Composites Sci. and Tech. 2003, 63, 2223-2253, (US Patent publication No. US20030137069).

Although there have been reports of the use of electrospun fibers as scaffolds for select drug delivery and biomaterials applications, the incorporation of bioactive molecules has not been widely exploited. In one example, tetracycline was included in a solution of poly(lactic acid) (PLLA) and poly(ethylene-co-vinyl acetate) and electrospun in a fiber membrane to study the release profile of the fiber-encapsulated drug. PLLA has also been studied as a matrix to incorporate the drugs rifampin (to treat tuberculosis) and paclitaxel (anticancer drug). Polymers loaded with both of these therapeutic molecules could be fabricated into nanometer to micron diameter electrospun PLLA fibers and used for delivery of the drug.

While the development of functionalized polymers that can elicit specific biological responses is of great interest in the biomedical community, as well as the development of methods to fabricate these biologically functionalized polymers, there is still a need for more facile methods to create biologically active functionalized matrices that permit immobilization and long-term delivery of biomolecules and other small functioning molecules, moieties, and/or particles.

For example, although there have been studies demonstrating the utility of functionalizing electrospun fibers, the functionalization of electrospun fibers to confer specific biological activity would be particularly advantageous for many biomaterial applications, as such modification would permit the fabrication of biomaterials that are structurally relevant and that possess properties designed to treat or address specific problems. In addition, such incorporation could serve to protect bioactive molecules, release them in relevant timeframe, and incorporate multiple such molecules. In particular, the development of simple methods to produce multifunctional electrospun fibers would advance the development of electrospun fibers for biomedical applications.

Of such bioactive molecules, glycosaminoglycans have been demonstrated to mediate a wide range of biological activities such as cell adhesion, cell mobility, cell proliferation and tissue morphogenesis via binding to various cell regulatory proteins such as the chemokines, growth factors, enzymes, enzyme inhibitors, and extracellular matrix proteins. The well studied glycosaminoglycan, heparin, is a linear, unbranched, highly sulfated polysaccharide chain, and it is well accepted that the electrostatic interactions between the sulfates of the glycosaminoglycan and basic residues of a protein play an important role in binding. In particular, the spatial orientation of the basic residues is a major determinant of heparin-binding ability, and variations in the pattern of the sulfation of the heterogeneous heparin therefore permit binding between heparin and a wide range of binding partners. Accordingly, heparin has been incorporated into covalent hydrogel delivery systems because of this ability to bind a diverse set of proteins. In addition, we and others have demonstrated that the interactions between heparin and specific HBPs can also mediate the assembly of noncovalently associated hydrogel networks (see, for example, N. Yamaguchi, K. L. Kiick, *Polysaccharide-poly (ethylene glycol) star copolymers as scaffolds for the production of bioactive hydrogels*, Biomacromolecules 6 (4) (2005) 1921-1930; N. Yamaguchi et al., *Rheological characterization of polysaccharide-poly (ethylene glycol) star copolymer hydrogels*, Biomacromolecules 6 (4) (2005) 1931-1940; B. L. Seal, A. Panitch, *Physical polymer matrices based on affinity interactions between peptides and polysaccharides*, Biomacromolecules 4 (6) (2003) 1572-1582).

Because hydrogels can mimic the high water content and mechanical properties of natural tissues, they are prime candidates as carriers of bioactive agents, in bioadhesive systems, or as biorecognizable materials. Given that poly (ethylene glycol), or PEG, is highly hydrophilic and generally nonadhesive to proteins or cells, it has found widespread use as a drug carrier, and many PEG hydrogels have been produced from aqueous solutions containing linear or branched PEG macromolecules via chemical crosslinking. In addition to hydrogels formed via radical crosslinking reactions, PEG hydrogels have been formed, for example, via Michael-type addition reactions upon mixing with thiol-bearing compounds or via the reaction between amino-terminated poly (ethylene glycol) and the herbal iridoid glycoside genipin. In some cases, cell adhesive peptide domains or biodegradable sequences have been introduced into PEG hydrogels to endow them with more biological signaling functions, including the capacity for growth factor delivery. Accordingly, there have been a variety of covalently crosslinked hydrogel systems developed to deliver growth factors via mechanisms such as diffusion and chemical or enzymatic reaction.

Noncovalent interactions provide an alternative method for crosslinking, as introduced above, removing the need for toxic chemical crosslinking agents in gel preparation. In addition, noncovalent crosslinking strategies may offer advantages in maintaining protein integrity and bioactivity until delivery. Polymer hydrogels have been formed via specific recognition events such as reversible antibody-antigen interactions (see T. Miyata et al., *A reversibly antigen-responsive hydrogel*, Nature 399 (6738) (1999) 766-769) and coiled-coil interactions (see for example, C. Y. Xu et al., *Reversible hydrogels from self-assembling genetically engineered protein block copolymers*, Biomacromolecules 6 (3) (2005) 1739-1749; C. Wang et al., *Hybrid hydrogels assembled from synthetic polymers and coiled-coil protein domains*, Nature 397 (6718) (1999) 417-420; W. A. Petka, et al., *Reversible hydrogels from self-assembling artificial proteins*, Science 281 (5375) (1998) 389-392). There has been little attention given, however, to the interaction between peptides (particularly coiled-coils) and polysaccharides in hydrogel assembly. Further, the fabrication of biologically active fibers through such functionalization strategies is a fairly new and unexplored area in the field of electrospinning, and electrospun fibers have not been investigated for their ability to incorporate growth factor binding glycosaminoglycans, such as heparin, in a manner designed to control release.

SUMMARY OF THE INVENTION

The invention is directed to a hydrogel comprising a polymer matrix comprising a noncovalent crosslink and a covalent crosslink, wherein the noncovalent crosslink comprises a first and a second PEG-LMWH conjugate and a heparin-binding compound, wherein the PEG molecule of each conjugate is covalently attached to the polymer matrix, and wherein the LMWH molecule of each conjugate is covalently attached to the PEG molecule of the same conjugate and noncovalently attached to the heparin-binding compound, and wherein the covalent crosslink comprises a first and a second PEG molecule and a LMWH molecule, wherein each PEG molecule is covalently attached to the polymer matrix and covalently attached to the LMWH molecule.

The invention is also directed to a hydrogel comprising a polymer matrix comprising a noncovalent crosslink and a covalent crosslink, wherein the noncovalent crosslink comprises a first and a second PEG-LMWH conjugate and a first heparin-binding compound, wherein the PEG molecule of each conjugate is covalently attached to the polymer matrix, and wherein the LMWH molecule of each conjugate is covalently attached to the PEG molecule of the same conjugate and noncovalently attached to the first heparin-binding compound, and wherein the covalent crosslink comprises either (i) a third and a fourth PEG-LMWH conjugate and a second heparin-binding compound, wherein the PEG molecule of each conjugate is covalently attached to the polymer matrix, wherein the LMWH molecule of each conjugate is covalently attached to the PEG molecule of the same conjugate, and wherein the LMWH molecule of each conjugate is either covalently attached to the second heparin-binding compound or wherein the LMWH molecule of the third conjugate is covalently attached and the LMWH molecule of the fourth conjugate is noncovalently attached to the second heparin-binding compound, or (ii) a first and a second PEG molecule and a third heparin-binding compound, wherein each PEG molecule is covalently attached to the polymer matrix and covalently attached to the third heparin-binding compound.

The hydrogels of the present invention may further comprise a second noncovalent crosslink, wherein the second noncovalent crosslink comprises a fifth and sixth PEG-LMWH conjugate, and a PEG-heparin-binding peptide conjugate wherein the PEG-heparin-binding peptide conjugate comprises two heparin-binding peptides that are covalently attached to the PEG molecule of the PEG-heparin-binding peptide conjugate, wherein the PEG molecule of each PEG-LMWH conjugate is covalently attached to the polymer matrix, wherein the LMWH molecule of each PEG-LMWH conjugate is covalently attached to the PEG molecule of the same conjugate, and wherein the LMWH molecule of each PEG-LMWH conjugate is noncovalently attached to a different heparin-binding peptide of the PEG-heparin-binding peptide conjugate.

BRIEF DESCRIPTION OF THE DRAWINGS

FIG. 1 is a scanning electron micrograph of PEO/LMWH-dye electrospun fibers.

FIG. 2 shows Laser Scanning Confocal Microscopy (LSCM) images of electrospun PEO fibers (a) transmitted light and (b) fluorescence (5 µm scale bar).

FIG. 10 shows scanning electron microscopy images of PEG-LMWH-dye/PLGA fibers and LMWH-dye/PLGA fibers after incubation in PBS for 6 h, 1 day, 3 days, and 14 days.

FIG. 11 shows retention of heparin within electrospun matrices as observed by multiphoton microscopy for the PEG-LMWH-dye/PLGA fibers and LMWH-dye/PLGA fibers after incubation in PBS for 6 h, 1 day, 3 days, and 14 days (10 µm scale bars).

FIG. 34 shows different crosslink embodiments of the present invention. An example of a covalent crosslink comprising PEG and LMWH is shown in A. An example of either covalent, noncovalent or a crosslink with a mixture of both covalent and non-covalent attachments is shown in B. The crosslinks in B comprise PEG, LMWH and a heparin-binding compound (HBC). An example of a noncovalent crosslink comprising PEG, LMWH and heparin-binding peptide is shown in C.

FIG. 35 shows additional example of crosslinked embodiments of the present invention. An example of a covalent crosslink comprising PEG and LMWH is shown in D wherein a heparin-binding compound is attached to the PEG. Another example of a covalent crosslink comprising PEG and a heparin-binding compound wherein a LMWH is attached to the PEG.

DETAILED DESCRIPTION OF THE INVENTION

Figure 3:
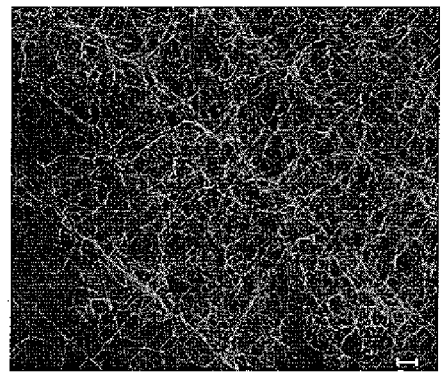
FIG. 3 is an LSCM image of electrospun PEO/LMWH-dye fibers (5 µm scale bar).
Figure 4:
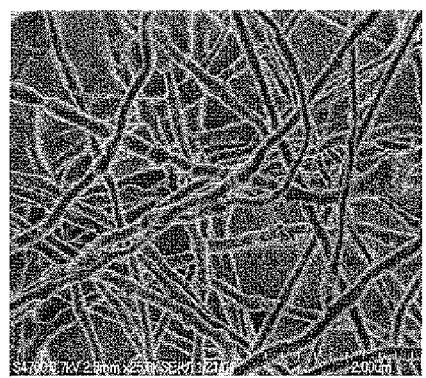
FIG. 4 is a scanning electron micrograph of electrospun PEO/PEG-LMWH-dye fibers.

The present invention relates generally to a composition and method for the formation of functionalized polymer matrices comprising a matrix polymer, a compatibilizing polymer and a biomolecule or other small functionalizing molecule. The invention is a novel strategy for the incorporation of low molecular weight, biologically active molecules (or molecules with other activities, e.g. sugars, peptides, polysaccharides, polypeptides, dyes, electroactive groups, etc.) into a fibrous or other matrix. The biological (or other) molecules are conjugated to an intermediate molecular weight polymer or "compatibilizing polymer" (e.g., but not limited to: linear, star, hyperbranched) to allow retention of the biomolecule in its bioactive form in fibers and other forms of polymeric materials (e.g. films, gels, solids, particles, etc.). Facile functionalization of electrospun fibers and other materials with other low molecular weight, bioactive polysaccharides and peptides (and other molecules) is contemplated by this invention. Such functionalization is important because biological processes are controlled via multiple and different signaling molecules that have distinct spatial and temporal release profiles, and the rate of their release from the fibers can be controlled with the technology of this invention.

The invention is currently demonstrated in a preferred embodiment comprising a low-molecular-weight-heparin (LMWH)-modified star copolymer incorporated into electrospun fibers. Attachment of active molecules to intermediate molecular weight polymers provides effective retention of the molecules in the material over time scales relevant for biological and other potential applications. The choice of intermediate molecular weight compatibilizing polymer will permit control over retention and release rate of the molecule or other active species.

Advantages of using a polymer-conjugated biomolecule (i.e. polymer conjugate) for incorporation of bioactive moieties into materials as provided by the invention, in place of covalent attachment of the biomolecule to a high molecular weight polymer used directly in material formation, are several-fold. For instance, they include i) the use of a polymer conjugate of the invention does not require a need for the development of distinct chemistry relevant for a particular molecule/polymer pair used in the material, as any polymer conjugate could be incorporated into any polymeric matrix; ii) the use of a polymer conjugate of the invention does not limit the number of molecules that could be incorporated into a given material for a given set of chemical transformations; iii) in biological applications, the incorporation of biomolecules via the current invention permits their controlled release in soluble form; iv) it is easier to control release rate and inclusion of multiple molecules at varying ratios/amounts than when a bio (or other) molecule must be covalently attached directly to the polymers of the material; and v) the incorporation of biomolecules into materials via this invention allows not only control over release rates, but permits facile incorporation of multiple biological (or other active) species into materials, and offers the potential for each species to have a separate and distinct release rate.

The materials may find application in drug delivery or tissue engineering scaffolds to promote tissue repair and/or regeneration. They could be useful in other materials in related applications where controlled release of a multiple of active ingredients is desired, e.g. biosensors, detoxification, DNA delivery, etc.

An important, overriding difference of the invention from the prior art is that it allows for molecules (e.g. growth factors, proteins, peptides, and other non-biological molecules, etc.) to be incorporated into a polymer matrix via compatibilization on of the molecules with the polymer matrix, and that it further allows for the controlled incorporation and release of a variety of different molecules from a polymeric matrix. For example, in the preferred embodiment (described in more detail in example 1), the incorporation of heparin, and more preferably LMWH, into an electrospun matrix via its attachment to a star PEG polymer provides increased growth factor binding to the electrospun matrix. The increased growth factor binding is due to the conjugation of LMWH to the PEG molecule. The PEG-LMWH molecule takes longer to diffuse out of the matrix, therefore allowing for more growth factor binding to occur within a given time period as shown by comparing the amount of growth factor binding to the PEG-LMWH matrix versus a matrix consisting of LMWH alone (See Example 1).

In the case of electrospun matrices, while there are limitations to what polymers can be electrospun, there are many possible uses. Solubility of fibers must be controlled, but such control is also possible with this invention as well as matching of mechanical properties for specific applications that are accomplished using appropriate choice of polymer, additives, and/or processing protocols.

Matrix Polymer

Matrix polymers, effective in this invention include but are not limited to: Nylon 6,6; Nylon 6,10; (other nylons, also), polyurethanes, polyacrylonitrile, polyvinyl alcohol, polylactic acid, polyethylene-co-vinyl acetate, polycarbonate, poly (iminocarbonate)s, polymethacrylates, poly(alkyl methacrylic acid)s, polyacrylates, poly(alkyl acrylic acid)s, poly (N,N'-diethylaminoethyl methacrylate), poly(N,N'-dialkylaminoalkyl acrylamides), poly(theylene oxide)/PEO, polyethylene terephthalate, polystyrene, polyvinyl chloride, poly vinyl phenol, polyacrylamide, poly(N-alkyl acrylamide)s, poly lactic-co-glycolic acids, polycaprolactone, poly(2-hydroxyethyl methacrylate) (polyHEMA), poly(vinylidene fluoride), poly(vinylidene chloride), poly(ethylene glycol)/PEG, polyvinyl pyrrolidone, polyethylene, polypropylene, poly(3-hydroxybutyrate), poly(ortho esters), polyanhydrides, poly(ether-ester) azopolymers, poly(dimethyl siloxane), poly(phosphazene)s, other copolymers of the above homopolymers (e.g. poly(methacrylic acid-co-ethylene glycol), and others.

Matrix polymers may also comprise natural polymers, such as collagen, silk, silk-like protein polymers, elastin, elastin-like protein polymers, poly(amino acids), cellulose acetate, hyaluronic acid, chitosan, fibronectin, and others.

Combination fibers comprising mixtures of different synthetic and/or natural polymers can also be prepared. Polymer combinations help to optimize solubility and mechanical properties of the fibers.

Composite materials comprising any of the above polymers and an appropriate inorganic matrix (clays, silicates, microparticles, etc.) can also be employed as a matrix polymer for applications requiring high mechanical strength, such as hard tissue engineering applications.

For drug delivery and biological applications, the following are particularly preferred: Poly(ethylene), poly(propylene), poly(vinyl chloride), poly(vinyl alcohol), polyethylene-vinyl acetate), poly(enol-ketone), poly(acrylic acids), poly(acrylamides), poly(N-alkyl acrylamides), poly(alkyl acrylates), PEG, PEO, poly(tetrafluoroethylene), poly(glycolic add), poly(lactic acid), poly(lactic-co-glycolic acid), poly(caprolactone), poly(3-hydroxybutyrate), poly(ortho esters), poly(anhydrides), poly(amido amines), poly(urethanes), poly(dimethyl siloxane), poly(phosphazenes), among others. In addition, collagen, silk, silk-like protein polymers, elastin, elastin-like protein polymers, poly(amino acids), cellulose acetate, hyaluronic acid, chitosan, fibronectin, and others, may also be used.

For applications in which a molecule is to be released in a non-biological environment (e.g., water purification, agricultural treatments, biosensors, smart fabrics, etc.), any of the above polymers could be employed; specific polymers would be chosen on the basis of the specific application.

Compatibilizing Polymer

Any moderate molecular weight polymer, of the chemical compositions of the above matrix polymers, that can be modified via reasonable chemical means with a biomolecule or other small functional molecule, moiety, or particle is considered a compatibilizing polymer according to this invention. Moderate molecular weight preferably comprises, but is not limited to, a molecular weight of approximately ½ to $\frac{1}{1000}$ the molecular weight of the matrix polymer it is bound to, in such a range that the compatibilizing polymer permits homogeneous incorporation of the biomolecule into the matrix polymer and sufficiently slows the diffusion-based release of the biomolecule over timescales relevant for a particular application. Some examples of moderate molecular weight polymers that would function effectively as a compatibilizing polymer in this invention include synthetic degradable polymers such as poly(glycolic acid), poly(lactic acid), poly(ethylene glycol) (PEG), poly(lactide-co-glycolide), and poly($\epsilon$-caprolactone) and others.

Additional polymers include polymers that could function as the matrix polymer, such as: poly(acrylic acids), poly(acrylamides), poly(N-alkyl acrylamides), poly(alkyl acrylates), poly(3-hydroxybutyrate), poly(ortho esters), poly(anhydrides), poly(amido amines), poly(urethanes), poly(dimethyl siloxane), poly(phosphazenes), among others. In addition, collagen, silk, silk-like protein polymers, elastin, elastin-like protein polymers, poly(amino acids), cellulose acetate, hyaluronic acid, chitosan, fibronectin, and others, may also be used. As the compatibilizing polymer can be functionalized at chemical groups located along the length of the polymer chain or at the termini of the polymer, many polymers can be employed. Potential additional polymers include: Nylon 6,6; Nylon 6,10; (other nylons, also), polyurethanes, polyacrylonitrile, polyvinyl alcohol, polyethylene-co-vinyl acetate, polycarbonate, poly(iminocarbonate)s, polymethacrylates, poly(alkyl methacrylic acid)s, polyacrylates, poly(alkyl acrylic acid)s, poly(N,N'-diethylaminoethyl methacrylate), poly(N,N'-dialkylaminoalkyl acrylamides), polyethylene terephthalate, polystyrene, polyvinyl chloride, poly vinyl phenol, polyacrylamide, poly(N-alkyl acrylamide)s, poly(2-hydroxyethyl methacrylate) (polyHEMA), poly(vinylidene fluoride), poly(vinylidene chloride), polyvinyl pyrrolidone, poly(3-hydroxybutyrate), polyanhydrides, poly(ether-ester) azopolymers, poly(dimethyl siloxane), poly(phosphazene)s, other copolymers of the above homopolymers (e.g. poly (methacrylic acid-co-ethylene glycol), and others.

A preferred compatibilizing polymer for use in this invention is poly (ethylene glycol) or PEG. PEG is a linear or branched neutral polyether with the chemical formula HO—(CH2CH2)n-H. PEG is highly soluble in water and many organic solvents (e.g., methylene chloride, ethanol, toluene, acetone, and chloroform), and is readily available in various sizes and functionalized architectures (e.g., amino-, carboxyl-, and sulfhydryl-terminated). Low-molecular weight (<100 daltons) PEGs are viscous and colorless liquids, whereas high-molecular weight PEGs are waxy solids whose melting points are proportional to their molecular weights with an upper limit near 67° C. PEG has been found to be nontoxic and is approved by the FDA for use in drugs (parentals, topicals, suppositories, nasal sprays), foods, and cosmetics. Molecular weights of PEG used in biomedical applications usually range between a few hundred to 20,000 Da. The molecular weight distribution of these PEG polymers is generally low, but the commonly used mono-methyl ethers of PEG exhibit broader molecular weight distributions. In solution, PEG is also a highly hydrated polymer, where each monomer (ethylene oxide unit) can bind three molecules of water. PEG polymer exhibits a large degree of segmental flexibility in aqueous solution and it is thought that PEG has the ability to influence the structure of several molecular layers of more loosely associated hydrating water molecules.

PEG is valued for its ability to exclude other polymers (natural and synthetic) from its presence in aqueous environment. This exclusion of other polymers is the primary driving force behind PEG's ability to reject proteins, from two-phase systems with other synthetic polymers, and makes this polymer both nonimmunogenic and nonantigenic. Because of its many benefits, PEG is ideally suited for protein modification. Indeed, PEG is currently considered one of the most successful techniques to prolong the residence time of protein drugs in the bloodstream. There are dozens of examples of PEG-protein conjugates described in the literature. For example, PEG has been considered a tool to enhance drug delivery to neoplastic tissues such as, for instance, pegylated proteins that have been applied in passive tumor-targeting while pegylated monoclonal antibodies or MoAb fragments have been investigated as immunotargeting agents. (see, for example Sato H., *Enzymatic procedure for site-specific pegylation of proteins*, ADVANCED DRUG DELIVERY REVIEWS 54 (4): 487-504 Jun. 17 2002; Deiters A., et al., *Site-specific PEGylation of proteins containing unnatural amino acids*, BIOORGANIC & MEDICINAL CHEMISTRY LETTERS 14 (23): 5743-5745 Dec. 6 2004; Hermanson, Greg T., Bioconjugate Techniques, 1$^{st}$ edition, Academic Press, New York, 1996) (All of which are herein incorporated by reference in their entirety).

PEG conjugation technology has been used, for example, to improve the therapeutic efficacy of recombinant human proteins because it alleviates many problems associated with therapeutic protein formulations. For example, the attachment of PEG to a protein affects its molecular size, charge, and receptor-binding capabilities, which can serve to decrease the conjugate's overall rate of clearance from the body. Also, by sterically shielding the protein domains susceptible to proteolytic attack, PEG decreases the protein degradation that causes protein biological inactivity. Finally, by sterically masking a therapeutic protein's immunogenic/antigenic determinants, PEG conjugation commonly results in conjugates that are nonimmunogenic and nonantigenic. The result of changes in the parental protein's characteristics by PEG almost invariably increases the plasma half-life and resistance to proteolytic degradation, and decreases immunogenicity and antigenicity of the resultant PEG-protein conjugate. Although PEG is generally considered to be non-immunogenic, its parenteral administration has been found to stimulate the production of antibodies.

Small Functioning Molecule

Small functioning molecules according to this invention include, but are not limited to, biomolecules and functional molecules such as peptides, sulfated peptides/polypeptides, peptides/polypeptides with other functionalization/modifications, peptides/polypeptides containing non-natural amino acids, polypeptides (natural AA, sulfated, non-natural AA, other modified side chains, etc.), protein fragments, proteins (e.g., growth factors, growth hormones, cytokines, insulin, etc.), enzymes, saccharides, oligosaccharides, polysaccharides, small molecule drugs (e.g., doxorubicin, aspirin, adriamycin, tetracycline (antibiotic), chloroquine (antimalarial), tamoxifen, and other small molecule drugs that can be chemically conjugated to a polymer), dyes, organics, metals, and nanoparticles and nanomolecules.

One particularly interesting biomolecule is heparin. Heparin is a highly sulfated glycosaminoglycan that binds or interacts with growth factors such as fibroblast growth factor (FGF), vascular endothelial growth factor (VEGF), heparin-binding epidermal growth factor (HBEGF), transforming growth factor-β (TGF-β), nerve growth factor (NGF), and others. Growth factor agonists and antagonists also bind or interact with heparin. Those having skill in the art are clearly aware that growth factors are important for controlling cellular activities such as cell growth and proliferation. The incorporation of heparin in the electrospun matrix is of functional importance owing to heparin's role as a binding site for many growth factors; sulfated peptides may have similar activity and would therefore also be useful for similar reasons. For example, the binding of growth factors to glycosaminoglycans in the ECM is essential for storage, release, and preservation of the bioactivity of the growth factor. Heparin primarily serves to immobilize growth factors until release but is also known to control their mitogenic activity, and in several cases, serves as a cofactor to promote binding of the growth factors to their receptors. Heparin is also known to regulate the growth of fibroblast and endothelial cells when combined with heparin-binding growth factors. For example, heparin has been reported to have been incorporated into a chitosan hydrogel where it was found to induce neovascularization in vivo and enhanced the activity of acidic fibroblast growth factor (aFGF) and basic fibroblast growth factor (bFGF) and stabilized the growth factors in vitro. A variety of other reports also confirm the benefits of including heparin in a bulk hydrogel matrices, such as those comprising fibrin, PEG, collagen, hyaluronic acid, and synthetic polymers, and the extension to a fibrous matrix may provide additional structural advantages for producing materials that mimic the ECM. Incorporation of biomolecules such as heparin, into a polymer matrix allows for the exploitation of heparin's affinity for growth factors as a strategy to deliver them from a fibrous ECM-mimetic matrix. Those having skill in the art understand that heparin binds a variety of proteins with disparate function. It is contemplated that any such protein would be a candidate for use in this invention.

Method of Formulating Functionalized Polymers

Some methods for processing polymers into a given form that can be applied in the invention for producing polymeric matrices capable of controlled release of the compatibilizing polymer/biomolecule conjugates include, for example, crosslinking of a polymer to form a hydrogel network can be employed; any method for crosslinking polymers can be applied for formation of the crosslinked network, using standard initiators or at least trifunctional monomers; standard free radical initiators include thermal initiators, redox initiators, photoinitiators; the inclusion of a bifunctional vinyl molecule with appropriate vinyl monomers would produce crosslinked networks of the vinyl matrix polymers.

Additionally, noncovalent methods of producing a crosslinked network could be employed. Such interactions include but are not limited to ionic crosslinking (e.g. alginate crosslinking via interaction with divalent cations, layer-by-layer deposition of polyelectrolytes, etc.), protein-protein interactions, peptide-saccharide interactions, saccharide-saccharide interactions, self-assembly of peptidic molecules, and antibody-antigen interactions. The pore size of the crosslinked network should be smaller than the size of the compatibilizing polymer/biomolecule conjugate in order to permit release of the biomolecule to be delayed via its conjugation to the compatibilizing polymer.

Any method of forming different three-dimensional particles and structures could also be applied in the current invention. For example, emulsion (or inverse emulsion) polymerizations, crosslinking (in colloidal suspensions, micellar or liposomal solutions, or emulsions), or spray crosslinking can be used to form particulate and nanoparticulate polymers. Crosslinking of monomer solutions in a mold or microfluidic channel permits the construction of a matrix of essentially any shape/size. Films cast of the monomer solutions (e.g., via spincoating, doctor blade application, dipcoating, etc.) can also be produced via crosslinking by any of the above mechanisms or via simple casting/drying of a non-water soluble polymer.

Electrostatic fiber spinning, or "electrospinning," is a preferred process for this invention. Electrospinning is a process by which superfine fibers, ranging from approximately 10 nanometers to about 10 microns in diameter, are formed. The resulting electrospun fiber web has a high specific surface area that is beneficial in a wide variety of technologies due to the small fiber diameter and its porous structure. A high voltage source is used during the electrospinning process to generate an electrically charged jet of polymer solution or melt expelled from a device such as a pipette. This process is then followed by a drawing of the resulting filaments as they solidify or coagulate. Electrospinning provides a simple approach for production of solid, as well as hollow, one-dimensional nanofibers from a variety of starting materials. To date, dozens of synthetic or natural polymers, melts, and polymer blends have been successfully spun using the electrospinning process. (see, for example, Shin et al., Biomaterials 2003, 24, 4353-4364; Sukigara et al, Polymer 2003, 44, 5721-5727 (Frank Ko); Li et al, J. Biomed. Mater. Res. 2002, 60, 613-621 (Frank Ko); Jin et al., Biomacromolecules 2002, 3, 1233-1239 (David Kaplan); Jin et al., Biomaterials, 2004, 25, 1039-1047 (David Kaplan); Farach-Carson, M. C.; Wagner, R. C.; Kiick, K. L., *Extracellular Matrix Structure, Function, and Applications to Tissue Engineering*, CRC Biomedical Engineering Handbook, CRC Press, New York, 2004; Huang et al., Composites Science and Technology 2003, 63, 2223-2253) (All said references are herein incorporated by reference in their entirety). A broad range of electrospun materials have been published and include synthetic polymers with electrical properties ranging from non-conducting polyurethane to conducting polyaniline, in addition to natural polymers such as collagen and silkworm silk. There is also much recent work on nanofibers electrospun from biocompatible or biodegradable polymers for bioengineering applications. The fibers may be made from a polymer solution via an electro spinning process as described in Reneker, U.S. Pat. Nos. 4,323,525, 4,689,525, US 20030195611, US 20040018226, and US 20010045547, which are incorporated herein by reference in their entirety. The specific types of polymers that may be produced in fiber form via the electrospinning process include those listed in Huang, US 20030195611, US 20040037813, US 20040038014, US 20040018226, US20040013873, US 2003021792, US 20030215624, US 20030195611, US 20030168756, US 20030106294, US 20020175449, US20020100725 and US20020084178 all of which are herein incorporated by reference in their entirety.

When constructing electrospun fibers for biomedical applications, certain material considerations must be acknowledged. Some minimal properties of a drug delivery system are that the material must be non-immunogenic, degradable with non-toxic products, able to be excreted from the body, and deliver therapeutic molecules in a controlled and predictable manner. Manufacturing time and complexity, along with handling, must also be considered. In compliance with these requirements, matrix polymers such as PEO and PLGA serve as excellent candidates for fabrication of the matrix via electrospinning; indeed, the successful use of these polymers in a variety of tissue engineering and drug delivery applications has been documented. Those having skill in the art are familiar with the processes used in tissue engineering and drug delivery as required for incorporation in this invention.

In addition to electrospinning, other traditional methods of making polymeric fibers can be applied, when possible, to the formation of active fibers of larger diameter. Given the choice of biomolecule or functional molecule or particle with a particular matrix polymer would dictate the use of solution spinning, melt spinning, or other spinning protocols.

Regarding the attachment of the biomolecule (or other small functioning molecules) to the compatibilizing polymer, the chemical reactions to be used are unlimited and are chosen based on the desired compatibilizing polymer/biomolecule combination. Initially, the matrix polymer composition may be altered for any given desired application and the combinations of matrix polymer/compatibilizing polymer/biomolecule for any application are limited only by the choice of a given application, not by the scope of the invention.

In a preferred embodiment, poly(ethylene glycol) (PEG) functionalized with low molecular weight heparin (PEG-LMWH), is fabricated into fibers for use in drug delivery, tissue engineering, or wound repair applications. In particular, a four-arm star PEG with covalently attached LMWH was found to be well suited for incorporation into electrospun fibers with matrix polymers such as PEO and PLGA. Further, the use of a PEG-LMWH conjugate proved to have a better effect on growth factor binding than when compared to free LMWH (see Example 1).

Interestingly, it was observed that the incorporation of heparin into the electrospun PEO and PLGA fibers did not affect the surface morphology or fiber diameters. The fibers produced had diameters ranging from approximately 100 nm to 400 nm. Our data indicates that PEG-LMWH conjugates can be incorporated into an electrospun matrix at concentrations ranging from 3.5 µg to 85 µg per milligram of electrospun fibers, although with greater heparin concentrations in the spinning solution, it should be feasible to produce higher levels of heparin loading in the fibers. Incorporation of PEG-LMWH into the matrix permits retention of the heparin for at least 14 days. Improvements in the binding of basic fibroblast growth factor (bFGF) to the electrospun fibers were also observed for fibers functionalized with PEG-LMWH over those functionalized with LMWH alone. The combination of these results suggests the utility for producing electrospun fibers that are appropriately functionalized for use in biomaterials applications.

Although LMWH was indicated to be incorporated into fibers with simple mixing in our investigation, the conjugation of LMWH to the star PEG slightly improved the amount of heparin incorporated into the fiber matrix and permitted a significantly improved amount of growth factor binding to these matrices, which was suggested to result from an improved retention of heparin in the fibers. If the use of such PEG-LMWH conjugates also slows the release of heparin over extended periods of time, it will allow for a slower, more sustained release of growth factor, which is often required to achieve desired biological outcomes.

The conjugation of heparin, and more preferably, LMWH, to a relatively short (relative to the matrix polymer molecular weight) polymeric chain therefore permits facile functionalization of fibers and also allows for retention and significantly slowed release of LMWH from the matrix over time. Given the importance of co-presentation of the LMWH with growth factors at the growth factor receptor these systems also offer the potential advantage of improving growth factor activity over systems in which heparin is covalently attached directly to the matrix and can therefore not be co-released with growth factor. The rate of release of heparin (and therefore growth factors) may also be modified via modifications in the polymer conjugate's molecular weight over a wide range, and coupled with the greater entanglement likely for flexible polymer chains, this may offer advantages over simple incorporation of a higher molecular weight heparin in fibers. In addition, the controlled incorporation and delivery of other and potentially smaller bioactive molecules, such as peptides, would also be widely possible via the incorporation of other similar PEG bioconjugates into these fibers. The ability to simply mix various PEG-conjugates in the electrospinning solution also offers advantages for creating multifunctional fibers.

The PEG-LMWH molecules used in these electrospinning studies have previously been demonstrated to be capable of sequestering growth factors in hydrogels and delivering them in bioactive form to induce proliferation of human umbilical vein endothelial cells. The amount of LMWH in these electrospun fiber matrices (3-86 μg) is also similar to that in hydrogels produced with these polymers; the hydrogels can effectively release bFGF for time periods of at least 16 days. These results therefore show significant promise for the potential of delivering similarly active growth factors from electrospun matrices. The additional advantage of the ease of mixing combinations of PEG-conjugates in the fibers is also promising for the facile production of multifunctional, non-immunogenic matrices for biomaterial applications.

It was found that LMWH functionalized PEG molecules can be easily incorporated into electrospun fibers. These fibers have nanometer scale diameters when electrospun using either PEO or PLGA as carrier polymers. The amount of LMWH per mg of fibers can range from 3.5-9.5 μg depending on the sample examined. Although both LMWH and PEG-LMWH can be processed into fibers, the incorporation of PEG-LMWH results in functional advantages such as improved growth factor binding, resulting from improvements in retention of the PEG-LMWH in the fibers over the LMWH alone. The PEG-LMWH can be retained in the fibers for at least 14 days, in contrast to LMWH, which is almost completely released from the fibers after 24 hours. A slower release of LMWH, and any coupled growth factors, allows for drug delivery over a period of time that more closely matches the time scales needed for tissue repair or regeneration should the fibers be used in biomedical applications. The use of electrospinning as the fabrication method for this biologically functionalized matrix is preferred due to its ability to allow for the incorporation of LMWH, ease of fabrication, fiber spinning at a variety of temperatures, and use of small amounts of material. The ability to scale electrospinning from the laboratory to the industrial scale offers opportunities to produce matrices for biomaterials applications. The electrospun matrix also meets many requirements in its porosity and 3-D nature to make the fibers suitable for drug targeting and tissue engineering applications. Such simple strategies for creating electrospun matrices that are both structurally relevant and biologically active could find increased utility in a variety of biomedical applications.

Functionalized Cross-Linked Matrices

In an alternative embodiment, the invention is directed to the use of a functionalized compatibilizing polymer in the production of materials in which assembly, mechanical response, and biological properties are controlled by protein-polysaccharide interactions. Such materials are designed to mimic the biological environment and find use in the delivery of growth factors.

Specifically, functionalized crosslinked matrices, such as hydrogels, capable of assembly by, for example, interactions between heparin and peptides, permit the formation of matrices that allow for effective protein delivery. For example, an elastic or viscoelastic hydrogel formed by the combination of a compatibilizing polymer-LMWH conjugate and a compatibilizing polymer-peptide conjugate is a preferred interaction contemplated herein. While the use of any compatibilizing polymer is contemplated, a preferred compatibilizing polymer for use in this embodiment would include PEG. Also, while preferred, it is not necessary that the compatibilizing polymer be the same for both the LMWH conjugate and the peptide conjugate.

In this particular embodiment, a hydrogel provides the benefits of controlling drug delivery rates by, for example, changing the heparin-binding peptide or manipulating the hydrogel's physical properties and erosion profiles.

In a specifically preferred embodiment (more fully described in Example 4) a heparin-binding, coiled coil peptide, $PF_4ZIP$, was employed to mediate the assembly of heparinized polymers. Heparin binding peptides (HBP) from antithrombin III and the heparin interacting protein have also been employed; any heparin-binding peptide with desired affinities can be used in the production of materials of this kind. Importantly, viscoelastic hydrogels were formed upon the association of $PF_4ZIP$-functionalized star poly(ethylene glycol) (PEG-$PF_4ZIP$) with low-molecular-weight heparin-functionalized star PEG (PEG-LMWH). The viscoelastic properties of the hydrogels can be altered via variations in the ratio of LMWH to $PF_4ZIP$ (or any HBP). Comparison of growth factor (bFGF) release profiles with the hydrogel erosion profiles indicates that bFGF delivery from this class of hydrogels is mainly an erosion-controlled process and the rates of bFGF release can be modulated via choice of HBP or via variations in the mechanical properties of the hydrogels. Manipulation of hydrogel physical properties and erosion profiles provides novel materials for controlled growth factor delivery and other biomedical applications.

Growth Factor-Cross-Linked Matrices

In even another alternative embodiment, the invention is directed to the use of a functionalized compatibilizing polymer to form a crosslinked matrix that comprises the combination of a compatibilizing polymer-biomolecule conjugate and a growth factor, wherein a biomolecule such as LMWH functions effectively. In such an embodiment, it is intended that the growth factor function as a cross link that eventually is removed and drug is released. Removal of the growth factor may result from passive release and/or targeted release via targeted ligand exchange of the growth factor with specific receptors on cell surfaces. The growth factor crosslink may also itself be the desired drug, or in certain cases, the PEG-LMWH polymer may have desired biological effect.

In a specifically preferred embodiment, PEG-LMWH can be mixed with vascular endothelial growth factor (VEGF) to form a viscoelastic hydrogel. Formation of a hydrogel occurs as a result of the binding of the heparin-binding VEGF, with multiple heparin binding sites, to the PEG-LMWH. While VEGF, a dimeric growth factor with two heparin-binding sites, is described, other methods for generating growth factors with multiple heparin binding sites could produce a growth factor capable of crosslinking PEG-LMWH polymers via noncovalent interactions (e.g. genetic mutation of growth factor genes to introduce additional heparin-binding sites in the growth factor, conjugation of multiple growth factors to a polymer, etc.). Noncovalently crosslinked PEG-LMWH/VEGF hydrogels are capable of releasing VEGF over periods spanning at least two weeks, and the release of VEGF (and resulting erosion of the network) is also responsive to the presence of the cell surface receptors for VEGF. Release of VEGF, and erosion of the network, can therefore be coupled and made responsive to the cellular environment. VEGF released from such assemblies causes increased proliferation of porcine aortic endothelial (PAE) cells, which confirms that the released VEGF is bioactive. Release of other growth factors via similar mechanisms should therefore also be possible to permit release of multiple, bioactive growth factors.

Although the invention is illustrated and described herein with reference to specific embodiments, the invention is not intended to be limited to the details shown. Rather, various modifications may be made in the details within the scope and range of equivalents of the claims and without departing from the invention.

EXAMPLES

Example 1

Electrospinning Functionalized Fibers
Materials and Methods

Hydroxy terminated and thiol terminated four-arm star poly(ethylene glycol)s ($M_n$=10,300; $M_w$=11,300 g/mol and $M_n$=10,000; $M_w$=10,800 g/mol, respectively) were purchased from Polymer Source (Dorval, QC, Canada). LMWH sodium salt (porcine intestinal mucosa, avg. molecular weight 3000 g/mol) was obtained from Sigma (St. Louis, Mo.). Alexa Fluor® 350 carboxylic acid, succinimidyl ester was obtained from Molecular Probes (Eugene, Oreg.). Solvents and reagents were distilled or purified according to standard procedures.
Synthesis of PEG-LMWH Conjugate
N-Deacetylation of LMWH.

LMWH ($M_r$=3000 g/mol) was used in these investigations. In some cases, the LMWH was first separated into a high affinity fraction via anionic exchange chromatography on diethyl aminoethyl (DEAE) resin. Such fractionation is not an absolute requirement, but provides a LMWH fraction with higher heparin binding affinity. LMWH was eluted from the column via gradient elution in Tris buffer (pH 7.5, 20 mM) with sodium chloride concentrations ranging from 0 to 2M. The late eluting fraction of LMWH was collected, dialyzed against several changes of deionized water (SpectraPor, MWCO 1000 Da), and lyophilized prior to use. The fractionated LMWH (250 mg), hydrazine (5.3 g), hydrazine sulfate (53 mg), and water (2.3 mL) were added to a heavy duty reaction vessel, and the reaction vessel was tightly capped and the mixture was stirred at 95° C. for 16 h. After the solvents were removed in vacuo, the product was dialyzed using a SpectraPor dialysis membrane (MWCO 1000 Da) first against 1 M NaCl and finally against water (for each dialysis bath was changed four times after 2, 8, 16, and 24 h) and lyophilized to afford a slightly yellowish solid, 153 mg (61% yield).
Synthesis of Maleimide and Alexa Fluor 350® Functionalized LMWH.

To a 10 mL vial were added N-deacetylated heparin (10 mg), dry dowex 50WX4-200 ion-exchange resin (strongly acidic cation), and anhydrous dimethylformamide (DMF, 4 mL) and the reaction mixture was stirred at room temperature until complete dissolution of heparin was observed. The resin was filtered and to the filtrate were added a few drops of anhydrous triethylamine and a solution of 4-(N-maleimidomethyl)cyclohexanecarboxylic acid N-hydroxysuccinimide ester (0.75 equiv.) (Sigma, St. Louis, Mo.) in anhydrous DMF (0.3 mL) and the reaction mixture was stirred at 60° C. for 20 h. To this mixture was added a solution of Alexa Fluor 350® carboxylic acid, succinimidyl ester (1 equiv.) in anhydrous DMF and the reaction mixture was further stirred at 60° C. for 20 h. The solvent was removed in vacuo to yield a slightly yellowish solid, which was redissolved in PBS (pH 6.5, 0.10 M, 0.15 M NaCl). After the insoluble particles were filtered, the filtrate was purified via fast protein liquid chromatography (FPLC) equipped with a Superdex 200 gel filtration column (Amersham, Piscataway, N.J.) using 0.2 M NaCl at 0.5 mL/min as eluting buffer. The heparin containing fractions were combined and dialyzed using a SpectraPor membrane (MWCO 1000 Da) first with 1 M NaCl and finally with water (each dialysis bath was changed four times after 2, 8, 16, and 24 h) and were then lyophilized to give a slightly yellowish solid, 4.2 mg; $^1$H NMR (400 MHz, $D_2O$, 29° C.): d=0.86-1.95 (10 H, cyclohexyl, m), 3.38-5.43 (72 H, heparin, m), and 6.84 ppm (2 H, —COCH=CHCO—, s).
Synthesis of PEG-LMWH.

To a 100 mL round bottom flask equipped with a $N_2$ inlet were added maleimide and dye-functionalized LMWH (120 mg) and PBS (10 mL, pH 6.5, 0.10 M, 0.15 M NaCl) and the solution was degassed by bubbling $N_2$ for 15 min. To this solution was slowly added a degassed solution of PBS containing thiol terminated four-arm star PEG (65 mg in 10 mL) and the reaction mixture was stirred at room temperature for 2 h. The reaction of the thiol was 96% complete as confirmed via analysis with Ellman's reagent. The reaction mixture was quenched by adding a solution of N-ethylmaleimide (12 mg) in DMF (0.4 mL). The crude product was purified via FPLC with a Superdex 200 gel filtration column (Amersham, Piscataway, N.J.) at 0.5 mL/min using 0.2 M NaCl as eluting buffer. The product isolated by FPLC was purified via dialysis against water (water bath was changed four times after 2, 8, 16, and 24 h) and lyophilized to give a slightly yellowish solid, 150 mg; $^1$H NMR (400 MHz, $D_2O$, 29° C.): d=0.86-1.95 (40 H, cyclohexyl, m), 2.50-2.88 (12 H, —$COCH_2CHCO$—, m), 3.38-5.43 (288 H, heparin, m), and 3.70 ppm (908 H, PEG backbone, —$CH_2CH_2O$—, s). Integration of the $^1$H NMR spectrum suggests 73% functionalization of PEG with LMWH.
Electrospinning and Characterization
Fiber Spinning The electrospinning apparatus consisted of a syringe pump (Orion Sage™, Fisher, Fair Lawn, N.J.), high voltage supply (Glassman Series EH, High Bridge, N.J.), 1 mL syringe (Popper & Sons, New Hyde Park, N.Y.) and a needle (Hamilton, Reno, Nev.) with an inner diameter of 0.51 mm. A voltage of −12 kV was applied to the tip of the needle. A grounded metal sheet was used as the target and was positioned 15 cm from the tip of the needle for sample collection. The concentration of the polymeric solutions varied depending on the carrier polymer employed. PEO (BDH Chemicals, Poole, UK, $M_w$=300,000 g/mol) was used at a 10 wt % concentration in water and a flow rate of 0.07 mL/min was employed. PLGA (Sigma Aldrich, St. Louis, Mo., 75:25, $M_w$=90,000-126,000 g/mol) solutions were made at a 45 wt % concentration in DMF (Fisher, Fair Lawn, N.J.) and required a flow rate of 0.26 mL/hr.

Characterization

Figure 7:
FIG. 7 shows LSCM images of electrospun PLGA fibers (a) transmitted light and (b) fluorescence (10 µm scale bars).

The electrospun fibers were characterized via field emission scanning electron microscopy (FESEM) (Hitachi S-4700) coupled with the energy dispersive X-ray (EDX) (Oxford Inca X-Ray Microanalysis) for elemental analysis of electrospun fibers. Laser scanning confocal microscopy, LSCM, (Zeiss LSM 510 NLO) was used to observe the location of the heparin-bound dye. A fluorescence excitation wavelength of 747 nm and a KP685 filter were employed for these experiments. An oil immersion type Plan-Neofluar 40×/1.3 oil DIC (differential interference contrast) was used to obtain images in FIGS. 4, 5, 9, 10, 12 and a Plan-Apochrornat 63×/1.4 oil Ph3 (phase contract—the 3 denotes a specific condenser lens used) was used to collect the image in FIG. 7. A z-series was made for each sample at 0.8 or 1.0 μm sections.

Toluidine Blue Assays

To determine the amount of heparin in the electrospun fibers, a common colorimetric method employing toluidine blue was used. A toluidine blue solution was made by dissolving 25 mg toluidine blue (Sigma Aldrich, St. Louis, Mo.) and 1 g NaCl in 0.49 mL of 37% HCl and 50 mL of water. The toluidine blue that reacts with the heparin is removed from solution via extraction with hexanes (5 mL). The amount of unextracted toluidine blue remaining in the aqueous solution was determined by measuring the absorbance at 631 nm and, by difference, provides an estimate of the heparin concentration.

Samples were prepared by adding 1 mg of electrospun fibers to a solution consisting of 0.8 mL of toluidine blue solution and 2.5 mL of 0.1% NaCl. The test tube was vortexed and 5 mL of hexanes was added with additional vortexing. After 10 minutes, 120 μL of the toluidine blue solution was transferred into a cuvette and absorbance measurements were taken. The control samples consisted of 1 mg of either PEO or PLGA fibers, without heparin, to adjust for the amount of toluidine blue that may adhere to the fibers. Measurements were performed in duplicate.

Growth Factor Binding

Growth factor binding assays were employed to determine if the LMWH and PEG-LMWH electrospun samples were able to bind bFGF. All growth factor experiments were completed at room temperature in 24-well polystyrene assay plates (Corning Inc., Corning, N.Y.), blocked with 3% bovine serum albumin (BSA) (Sigma Aldrich, St. Louis, Mo.) in phosphate buffered saline (PBS) (Invitrogen, Carlsbad, Calif.). All electrospun samples were washed with PBS at room temperature. Samples were placed in the wells and incubated with 500 μL of a solution of basic fibroblast growth factor (bFGF, R&D Systems, Minneapolis, Minn., 10 ng/mL in PBS) for 2 h. After seven washes with 0.05 wt % Tween20 in PBS (PBS-T), 500 μL of a solution of bFGF antibody was added (R&D Systems, Minneapolis, Minn., 2 μg/mL in PBS) and incubated for 2 h. The samples were washed seven more times with PBS-T. The samples were then incubated for 30 min. in a 500 μL solution consisting of 1 μL horseradish peroxidase conjugated NeutrAvidin (Pierce, Rockford, Ill., 1 mg/mL), 8 mL PBS, and 2 mL SuperBlock™ Blocking Buffer (Pierce, Rockford, Ill.). The fibers were then washed seven times with PBS-T and incubated in 500 μL of TMB substrate solution (Pierce, Rockford, Ill.) for 10-12 mins. Absorbance at 450 nm was measured. All absorbance values were normalized with respect to a well treated with bFGF and antibody, as explained previously, but without any electrospun fibers. The growth factor binding assay was completed three times and the average values are reported.

Results

Electrospinning Physical Mixtures (1:4) of LMWH and PEO

A 1:4 LMWH to PEO mixture (25 mg LMWH and 100 mg PEO) was dissolved in water and electrospun. The fibers resembled typical electrospun PEO fibers with an approximate diameter of 100-400 nm and were slightly beaded. The presence of microspheres with an average diameter of 1-5 μm was also observed. Two control solutions were made. One control consisted of a 10 wt % PEO/$H_2O$ and the other a 10 wt % LMWH/$H_2O$. The 10 wt % PEO/$H_2O$ solution electrospun to form PEO fibers with a diameter of 100-400 nm. The fibers were circular in their shape and contained beads (200-600 nm in diameter) but no microspheres were observed. The 10 wt % LMWH/$H_2O$ control did not form fibers or microspheres, which is almost certainly due to the lack of entanglements in the negatively charged LMWH (3,000 g/mol). Attempts to electrospin higher MW heparin (12,000 g/mol) also failed for similar reasons.

Toluidine blue assays were performed on the electrospun physical mixtures of PEO and LMWH to determine if LMWH was present in the sample. It was found that 86 μg (+/−7.15) of LMWH was present per mg of electrospun fibers. The presence of LMWH indicated by the toluidine blue assay is consistent with the presence of LMWH in the matrix.

EDX was employed to determine the location of the heparin in the fiber matrix via detection of sulfur on the sulfated heparin; the results of the EDX analysis are outlined in Table 1. The presence of aluminum in the sample is due to the aluminum SEM mount used to hold the fibers. PEO fibers served as a control for this experiment; EDX detected 46% C, 5% O, and 49% Al in the PEO fibers, consistent with the composition of PEO. The significant amount of C detected was most likely to due to carbon adhesive tab that was used to secure the fibers for imaging. A thin film was cast of 10 wt % LMWH/$H_2O$ and used as the second control The atomic composition detected via EDX was 23% C, 40% O, 17% S, and 18% Na, consistent with the presence of LMWH in the sample (sodium is the counterion for the LMWH used in these studies). The 1:4 LMWH:PEO electrospun sample was tested in three different areas: the fiber portion, bead portion, and the microsphere. The fibers contained 42% C, 5% O, and 59% Al. Since no sulfur or sodium was detected, the results suggest that either the fiber section of the matrix consists of primarily PEO or that the concentration of sulfur is too low for detection via EDX. Generally, the lower limit of detection for EDX is approximately 1%, so it is possible that the LMWH may be incorporated into the fibers but at a concentration much lower than 1%. The beaded section of the matrix was found to contain 61% C, 13% O, 26% Al, and 0.3% S. The detection of the sulfur indicates that LMWH is present, at low concentrations, in the beaded areas of the electrospun mat. The microspheres were shown to contain 73% C, 20% O, 4% Al, 1.2% S, and 1.4% Na. The presence of sulfur and sodium imply that LMWH is present in the microspheres at higher concentrations than found in the beaded sections of the mat. The EDX results are consistent with the expected composition of the fibers, and the varying amount of sulfur in the different regions suggests that LMWH is not uniformly incorporated into the fibers via simple mixing.

TABLE 1

Average elemental composition of electrospun samples as determined by EDX (compositions are represented in atomic weight percent)

| Sample | C (%) | O (%) | Al (%) | S (%) | Na (%) |
| --- | --- | --- | --- | --- | --- |
| PEO Fibers | 46 ± 14.7 | 5.0 ± 1.15 | 49 ± 14.2 | ND* | ND |
| LMWH Film | 23 ± 1.63 | 40 ± 2.16 | ND | 17 ± 1.41 | 18 ± 2.50 |
| 1:4 LMWH:PEO | | | | | |
| fiber section: | 42 ± 9.02 | 5.0 ± 0.577 | 59 ± 18.9 | ND | ND |
| bead section: | 61 ± 2.65 | 13 ± 2.31 | 26 ± 4.51 | 0.3 ± 0.025 | ND |
| microsphere section: | 73 ± 2.52 | 20 ± 5.13 | 4.0 ± 1.66 | 1.2 ± 0.48 | 1.4 ± 0.13 |

*ND = not detected

Electrospinning Dye-Labeled LMWH with PEO

To visually map the location of the LMWH throughout the electrospun mat, a fluorescent dye, Alexa Fluor 350®, was covalently attached to LMWH, and the fibers were analyzed via LSCM; observation of fluorescence permits direct observation of the presence and location of LMWH throughout the electrospun matrix. PEO (10 wt %) was mixed with Alexa Fluor 350®-labeled LMWH (0.2 wt %) and electrospun. FIG. 1 shows resulting fibers with diameters of approximately 100-200 nm, with a few very large beads approximately 6 μm in diameter.

The fibers were then analyzed via LSCM to determine if the LMWH-dye molecules were incorporated into the matrix and to determine their distribution in the matrix. Electrospun PEO fibers were used as a control; results for the control are shown in FIG. 2. FIG. 2a shows data in reflection mode and confirms that fibers were present on the glass coverslip. FIG. 2b shows two small areas of fluorescence that are likely impurities in the PEO or dust in the sample, but confirms the complete lack of background fluorescence in the PEO fibers.

FIG. 3 presents LSCM data for electrospun fibers of the LMWH-dye/PEO mixture. The results demonstrate the fluorescence of the fibers, indicating the presence of LMWH. In contrast to SEM and EDX results, the LSCM results also suggest that the LMWH-dye is present not only in the beaded sections of the matrix, but also in the fiber regions. FIG. 3 shows the fluorescence of the fibers due to LMWH-dye incorporation. Z-stack images were also taken (not shown) to ensure that the LMWH-dye is present throughout the entire depth of the matrix and is not localized in any one area. Due to the LSCM limit of resolution, approximately 200 nm, the exact location of the heparin within each individual fiber is unknown. However, all LSCM images indicate that LMWH is present throughout the depths of the electrospun matrix, suggesting a fairly uniform dispersion of LMWH. Measurement of LMWH via toluidine blue assay confirmed the presence of approximately 4.3 μg (+/−0.923) of LMWH per mg of electrospun sample. A direct comparison cannot be made between the amount of LMWH in this sample and the amount in the physical mixtures of LMWH and PEO due to differing amounts of LMWH in the initial solutions. Nevertheless, these results suggest the opportunities for facile incorporation of bioactive polysaccharides into electrospun matrices.

Incorporation of PEG-LMWH-Dye in PEO for Electrospinning

Figure 6:
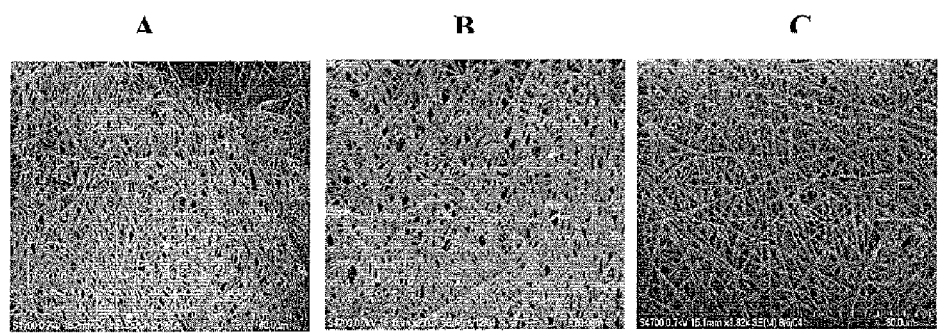
FIG. 6 shows scanning electron micrographs of (a) PLGA electrospun fibers, (b) PLGA/LMWH-dye fibers, and (c) PLGA/PEG-LMWH-dye fibers.

LMWH was covalently attached to the termini of a 4-arm star PEG and evaluated for its incorporation into an electrospun matrix. PEG-LMWH-dye (0.2 wt %) was mixed with PEO (10 wt %) in water. The electrospun fibers from this solution were analyzed via FESEM, with results shown in FIG. 6. As is shown in FIG. 6, the resulting fibers were 100-300 nm in diameter with the presence of microspheres (1-3 μm). The morphology of the PEG-LMWH fibers was very similar to those produced from the earlier samples with free LMWH. In both electrospun mats, fibers are in the nanometer size range and the onset of bead formation is observed by the roughness of the fibers (see FIGS. 1 and 4).

Figure 5:
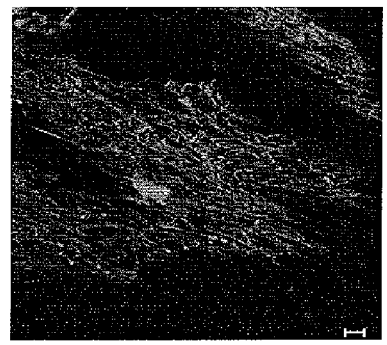
FIG. 5 is an LSCM image of PEG-LMWH-dye/PEO electrospun fibers (5 µm scale bar). Dark and colored regions are caused by folds in the surface of the macroscopic sample; not by composition variations.

The fiber matrix was then analyzed via LSCM to confirm that the PEG-LMWH-dye molecule was incorporated in the electrospun fibers; representative results are shown in FIG. 5. Similar to the results in FIG. 3, the data shown here also indicate that the fibers are evenly fluorescent across the matrix, showing that the PEG-LMWH was evenly distributed in the PEO fiber matrix. These fibers were found to contain 3.5 μg (+/−0.397) of heparin per mg of electrospun fibers. These results indicate a slight improvement in LMWH incorporation in comparison to the LMWH/PEO fibers, and may suggest that PEG-LMWH permits the incorporation of slightly more heparin than in the fibers produced using free heparin.

Changing the Matrix Polymer

Multiple polymers could be used as the matrix polymer. PLGA was chosen as an alternate carrier polymer for the LMWH systems due to the success of PLGA in biomaterial applications. PLGA/DMF (45 wt %) was electrospun with LMWH-dye (0.2 wt %) and also with PEG-LMWH-dye (0.2 wt %). Due to differences in molecular weight and viscosity, the concentration of carrier polymer is different than those used for PEO electrospinning, but all other processing conditions remained the same. The electrospun PLGA fibers are approximately 400-800 nm in diameter, (FIG. 6a). SEM revealed that fiber morphology was not affected by the incorporation of LMWH-dye or PEG-LMWH-dye, (FIGS. 6b and 6c).

Figure 8:
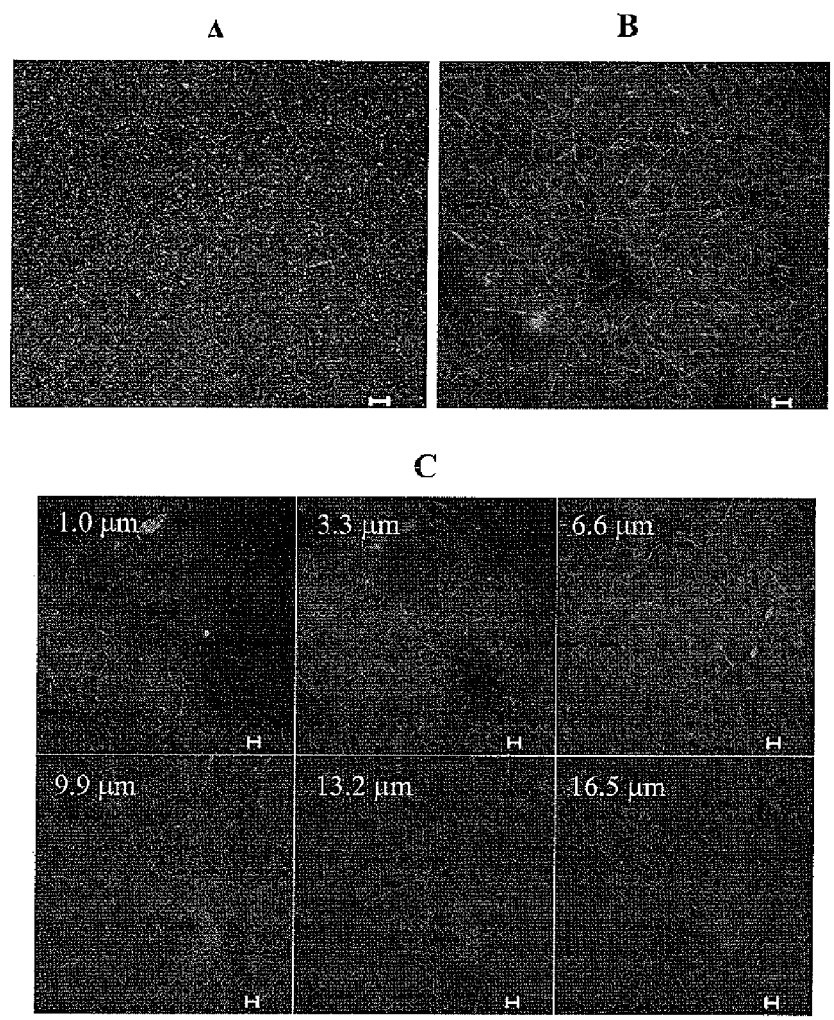
FIG. 8 shows LSCM images of electrospun (a) LMWH-dye/PLGA fibers and (b) PEG-LMWH-dye/PGLA fibers and (c) z-stack of PEG-LMWH/PLGA fibers (10 µm scale bars).

LSCM showed that the PLGA electrospun mat, shown in FIG. 7a under transmitted light, does not fluoresce to any significant extent. As encountered previously with PEO fibers, there is a small area of fluorescence in FIG. 7b, which is likely due to polymer impurities or dust on the sample. The images shown in FIG. 8 reveal that both LMWH-dye and PEG-LMWH-dye were incorporated into the PLGA matrix and z-stack LSCM images confirm that the heparin is present throughout the depths of the matrices. The toluidine blue assay indicated that there is approximately 8.41 μg (+/−0.532) of LMWH present per mg of electrospun LMWH/PLGA sample. The PEG-LMWH/PLGA sample contained 9.50 μg (+/−0.382) of LMWH per mg of electrospun fibers. The results of the FESEM, LSCM, and the toluidine blue assays suggest that the carrier polymer can be changed without affecting the incorporation of heparin or fiber morphology.

Example 2

Growth Factor Release Assays of Electrospun Fibers

An ELISA format was employed to characterize the binding of bFGF in a series of samples: a blank well, PLGA fibers alone, LMWH/PLGA fibers, and PEG-LMWH/PLGA fibers. Growth factor release studies were performed using a Quantikine Human FGF Basic Kit (R&D Systems, Minneapolis, Minn.). Incubation of the growth factor was completed using a 24-well polystyrene plate (Corning Inc., Corning, N.Y.) and transwell membranes (Fisher Scientific, Atlanta, Ga., 8 μm pore size) were used to secure the fibers during the release study. The plate, membranes, and fibers were blocked with 3% BSA (Sigma Aldrich, St. Louis, Mo.) in PBS (Invitrogen, Carlsbad, Calif.) overnight. All samples were washed three times with PBS at room temperature and then incubated with 4 μL bFGF (R&D Systems, Minneapolis, Minn., 2.5 μg/mL in PBS) for 2 h at 4° C. The fibers were then transferred to the transwell membrane and 1 mL of PBS was added and incubated at 4° C., unless otherwise indicated, for a specified amount of time. The wells were replenished with fresh PBS after each aliquot was removed. The amount of bFGF present in the matrix was determined via use of a standard spectrophotometric immunochemical assay following the protocols of the manufacturer (R&D Systems, Minneapolis, Minn.). Slight variations of the procedure could be necessary depending on the composition of the matrix.

Figure 9:
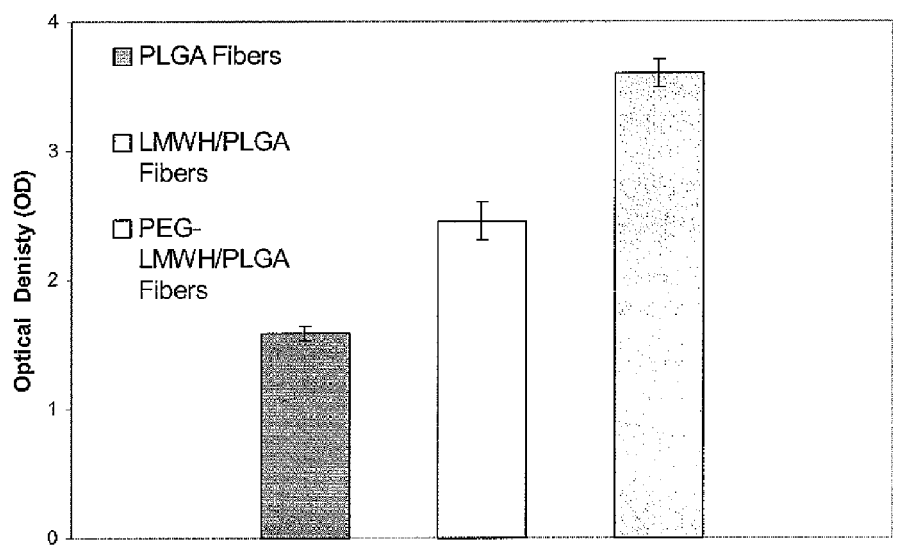
FIG. 9 shows bFGF binding on electrospun fibers. Each bar indicates±standard deviation of the average of three measurements.
Figure 12:
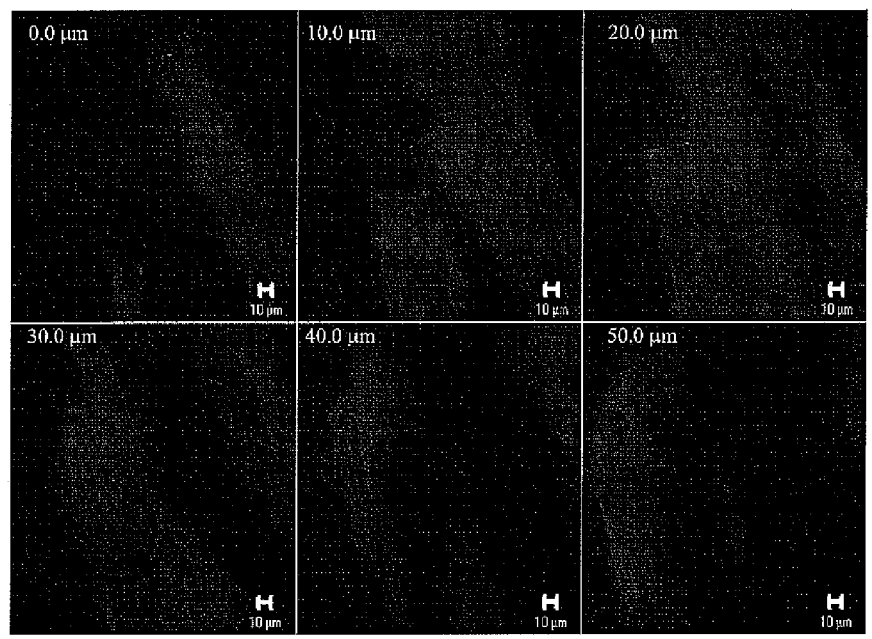
FIG. 12 shows retention of PEG-LMWH-dye within depth of the electrospun matrix after 14 days of incubation in PBS as imaged via multiphoton microscopy.

The optical density measurements, at a wavelength of 450 nm, resulted in the following absorbance values relative to the control (increasing absorbance values correlate with increasing growth factor binding): PLGA fibers 1.59 (+/−0.055), LMWH/PLGA fibers 2.46 (+/−0.146), and PEG-LMWH/PLGA fibers 3.59 (+/−0.106). FIG. 9 shows that there are significant differences in bFGF binding between the LMWH/PLGA and PEG-LMWH/PLGA fibers, despite the fact that the toluidine blue assays show that the two matrices contain similar amounts of LMWH after electrospinning. Since both the LMWH and PEG-LMWH samples began with similar amounts of heparin but did not exhibit the same level of bFGF binding, these data suggest that the PEG-LMWH may be retained in the electrospun fibers more effectively than LMWH alone. FESEM characterization of the electrospun membranes after the growth factor binding assay revealed that the PLGA fibers exhibited no visible signs of degradation during the time frame of the growth factor binding study (FIG. 10, parts a and b). This observation corroborates the fact that differences in growth factor binding likely result from differential LMWH retention rather than from variations in fiber degradation between samples. These electrospun membranes were also incubated in PBS for an additional 1 day, 3 days, and 14 days to determine if any fiber degradation occurred (FIG. 10, parts c-h). These SEM images show that there are no visible signs of fiber degradation for the time period studied in this investigation.

Figure 13:
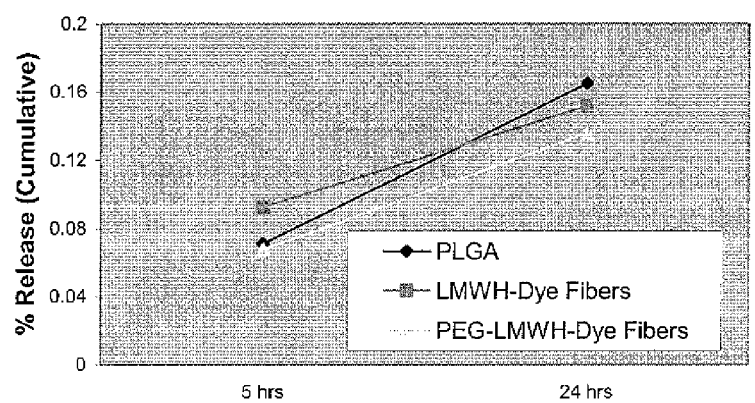
FIG. 13 depicts the release of bFGF from PLGA, LMWH-Dye, and PEG-LMWH-Dye electrospun fibers after 5 h and 24 h incubation in PBS.
Figure 14:
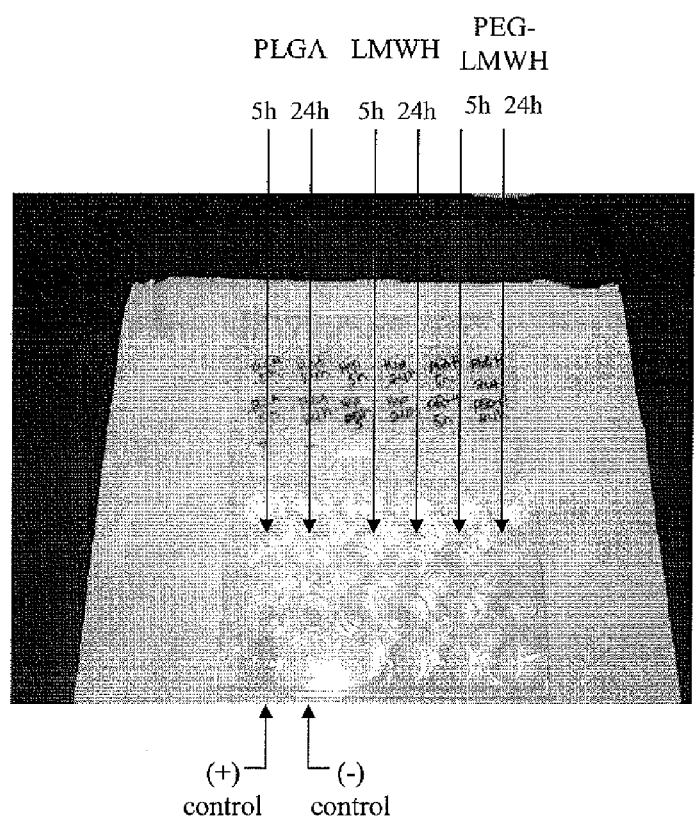
FIG. 14 is a digital picture displaying the visual differences observed in the binding of bFGF to PLGA, LMWH-Dye, and PEG-LMWH-Dye electrospun fibers after 5 h and 24 h incubation in PBS.

Characterization of the fibers after completion of the growth factor binding assays was conducted via multiphoton microscopy FIG. 11, parts a and b, shows the LMWH retention within the electrospun fibers after the growth factor assay, or 6 h of PBS incubation. After only 6 h in PBS, slight differences in the amount of LMWH within the fibers were observed via multiphoton microscopy; these differences were much more pronounced with an additional 24 h incubation in PBS (FIG. 11, parts c and d). In FIG. 11, parts e-h, the multiphoton images are shown in fluorescence and reflection mode. This was necessary due to the small amount of fluorescence in the samples in order to prove that fibers are present. In FIG. 11, parts g and h, the most visible differences are observed. After 14 days incubation in PBS, the PEG-LMWH-dye fibers still exhibit a moderate level of fluorescence in comparison to the LMWH-dye fibers, which show minimal signs of fluorescence. The differences in the amount of LMWH retained in the fibers were also observed throughout the depth of the matrix, as confirmed via z-stack images (see FIG. 12 for a representative z-stack image of PEG-LMWH-dye fibers after 14 days incubation in PBS).

bFGF release experiments were conducted with the 0.2 wt % LMWH-dye and PEG-LMWH-dye fibers over a 24 h period. As seen in FIG. 13, the release of LMWH-dye, PEG-LMWH-dye, and the PLGA control all exhibited less than 1% release of bFGF. This study was repeated to monitor the release over a 21 day period, assuming that the low release rates were due to the short incubation time of 24 h. However, the 21 day release consistently showed less than 1% bFGF release for all samples. Similar results were obtained in release studies conducted at 37° C. In order to determine if any bFGF remained in the electrospun matrices after these release studies, a binding study was completed on the 0.2 wt % heparin-containing fibers after 5 h and 24 h release in PBS. FIG. 14 is a digital picture showing the visual differences in the binding of bFGF to the fibers. The more intense the blue color, the more bFGF present. This picture clearly shows dramatic differences in binding to the PEG-LMWH fibers versus LMWH and PLGA only fibers. However, more LMWH is present in the PEG-LMWH-dye fibers. This suggests that either 1) more bFGF is retained in the PEG-LMWH-dye fibers due to the reduced diffusion times of the PEG-LMWH-dye complex or 2) all fibers may contain similar amounts of residual bFGF but the PEG-LMWH-dye fibers protect the structure of the bFGF and, thus, apparently more growth factor is detected by the immunochemical assay.

Example 3

Cell Proliferation Assay

The PEG-LMWH/PLGA, LMWH/PLGA, and PLGA fiber matrices were tested to determine if there were any differences in the ability of the membranes to affect cellular proliferation of MG63 (human osteosarcoma) cells. PLGA, LMWH/PLGA, and PEG-LMWH/PLGA electrospun membranes were sterilized under UV light for 4 h and incubated in 1.5 mL Dulbecco's Modified Eagle Medium (DMEM) containing 5% (v/v) fetal calf serum (FCS), bFGF (10 ng/mL), penicillin (100 U/mL) and streptomycin sulfate (100 μg/mL) for 2 h. The membranes were then washed 2-3 times with sterile PBS. All membranes were incubated in bFGF (15 ng/membrane) prior to the cell proliferation assay. The membranes were then placed in 24-well tissue culture dishes containing an MG63 cell (2×105 cells/mL, American Type Culture Collection, Manassas, Va.) suspension in DMEM supplemented with 5% (v/v) FCS. The plates were shaken every 30 min for 4 h. The scaffolds were then transferred to a new 24-well plate and incubated in DMEM containing 1% (v/v) FCS at 37° C. in an atmosphere of 95% air and 5% $CO_2$. Culture medium containing 1% (v/v) FCS was changed every 3 days. Cultures were terminated on days 1, 3, 6, 9, 12, and 15. MG63 proliferation was determined by immunodetection of bromodeoxyuridine (BrdU) incorporation (Cell Proliferation ELISA Biotrak System, Amersham Biosciences, Piscataway, N.J.), according to the manufacturer's instructions. Cells seeded on the electrospun membranes were labeled with BrdU and then incubated with peroxidase-labeled anti-BrdU antibody. Excess anti-BrdU antibody was removed by washing the membranes with washing buffer in a vortex mixer. The membranes were then incubated in TMB substrate to produce a colored solution. A plate reader was employed with detection at 450 nm to obtain optical density measurements. Three fiber membranes per sample were tested each day.

Figure 15:
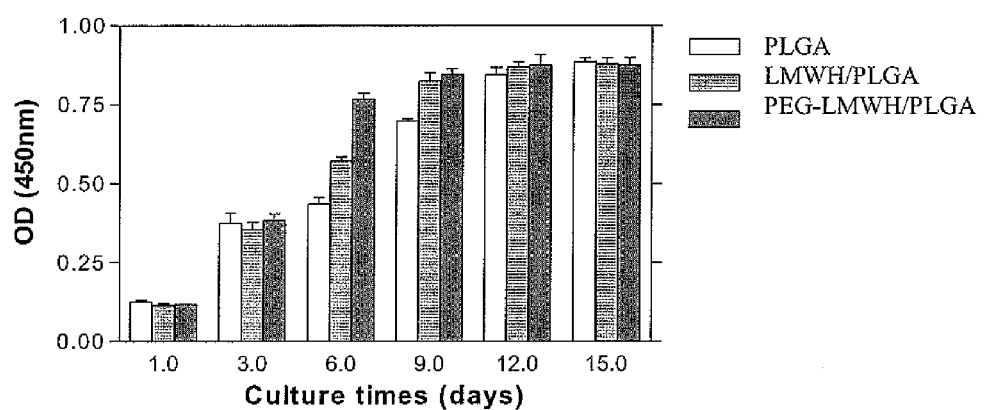
FIG. 15 shows the results from the BrdU cell proliferation assay. Each bar indicates±standard deviation of the average of three measurements.
Figure 16:
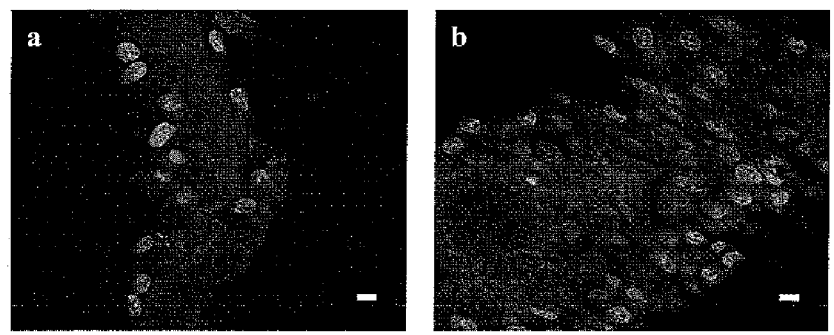
FIG. 16 provides LSCM images of (a) LMWH/PLGA and (b) PEG-LMWH/PLGA fibers (blue) incubated for 8 days with MG63 cells (green) (10 µm scale bars).

FIG. 15 illustrates the differences in cellular proliferation on PLGA, LMWH/PLGA, and PEG-LMWH/PLGA membranes. It was expected that cell proliferation would occur on all the samples tested due to the biocompatibility of PLGA, however, our interest was to determine which samples reached maximum cell proliferation first. The most significant differences were observed on day 6 where PEG-LMWH membranes exhibit significantly higher cell proliferation and therefore reached saturation before LMWH/PLGA or PLGA alone. FIG. 16 shows LSCM images of the cells (dyed green using a syto 13 stain) on electrospun LMWH or PEG-LMWH fibers (fluorescing blue due to the dye attached to the heparin). FIG. 16b shows that more cells are present on the PEG-LMWH/PLGA matrix and the image suggests that more cells penetrate the PEG-LMWH matrix (FIG. 16b) when compared to the LMWH fibers alone (FIG. 16a). These images illustrate the differences in cellular proliferation due to the presence of PEG-LMWH. Based on the results of this cellular assay it is believed that PEG-LMWH increases the rate of cell proliferation in comparison to the other samples due to the retention of PEG-LMWH in the matrix that causes increased retention and slower release of bFGF, which has been suggested in previous results presented in FIG. 14. The increased retention of bFGF may support higher cell proliferation rates. Although this was a very preliminary cell study, it does indicate that there are functional differences between electrospun matrices functionalized with either PEG-LMWH or LMWH alone.

Example 4

Functionalized Cross-linked Matrices
Materials

All materials were obtained and purified as described in Example 1.
Methods
Synthesis of PEG-LMWH Conjugates The synthesis of the PEG-LMWH conjugate exploited in hydrogel assembly was conducted via Michael-type addition reactions between maleimide functionalized heparin and thiol-terminated four-arm star PEG, as described in Example 1. The degree of LMWH functionalization in PEG-LMWH was determined to be 81% via $^1$H NMR spectroscopy. Synthesis of PEG-LMWH-Alexa Fluor 350 was conducted via similar protocols as previously described in the art.
Synthesis of PEG-HBP Conjugates All HBPs were prepared on Rink Amide MBHA resin via solid phase peptide synthesis with Fmoc-protection using a PTI PS3 peptide synthesizer (Protein Technologies Inc, Tucson, Ariz.) and purified via preparative-scale reverse-phase HPLC. The $PF_4ZIP$ sequence CGGRMKQLED-KVKKLLKKNYHLENEVARLKKLVG (SEQ ID NO:1) is based on a $GCN_4$ coiled coil and mimics the heparin-binding domain of human platelet factor 4. The heparin-binding peptides, ATIII and HIP, from antithrombin III (ATIII) and heparin interacting protein (HIP), have sequences of CKbAFAK-LAARLYRKA (SEQ ID NO:2) and CRPKAKAKAKAKDQTK (SEQ ID NO:3), respectively. Any heparin-binding peptide of sufficient affinity and appropriately slow dissociation (from heparin) would be equally applicable for use in these hydrogels. Peptides isolated as single fractions via HPLC were characterized via MALDI and ESI mass spectrometry. The mass of the purified HBPs was confirmed via ESI mass spectrometry. For example, for $PF_4ZIP$, m/z=992.5 [(M+4H)4+, calc'd 992.0] and m/z=1322.9 [(M+3H)3+, calc'd 1322.7]. Similar agreement between theoretical and observed mass values was observed for all other HBPs.

The synthesis of the PEG-HBP conjugates utilized in hydrogel assembly was conducted via Michael addition reactions between vinyl sulfone-terminated four-arm PEG and cysteine-terminated PF4ZIP peptide.
Characterization Peptides, PEG-LMWH, and PEG-HBPs were characterized via $^1$H NMR spectroscopy and MALDI-TOF Mass Spectrometry to determine purity, composition, and degree of functionalization.
Circular Dichroic Spectroscopy (CD)

CD spectra were measured at 5° C. to 75° C. on a Jasco J-810 spectropolarimeter (Jasco Inc, Easton, Md.) equipped with a Jasco PTC-424S temperature controller. Samples were equilibrated at the desired temperature for 30 minutes prior to data collection; equilibration was indicated by the absence of further changes in the CD signal at longer equilibration times. All CD spectra were taken in a 1 mm path length quartz cuvette, at wavelengths from 200 to 250 nm. Data points were recorded at every nanometer with a 4.0 s response time. The concentrations of peptide samples were determined via amino acid analysis for calculation of mean residue ellipticities.
Heparin Affinity Measurements Heparin-sepharose affinity liquid chromatography was performed on an ÄKTA Explorer FPLC equipped with a HiTrap Heparin HP column (5 ml, ~10 mg heparin/ml gel, Amersham Biosciences Corp, Piscataway, N.J.). Surface Plasmon Resonance (SPR). SPR sensorgrams were recorded on a BiaCore 3000 instrument (Biacore Inc, Piscataway, N.J.), employing a high-capacity LMWH surface created on a commercially available streptavidin-coated chip via treatment with biotinylated LMWH.
Bulk Rheology Experiments Bulk rheology experiments of the PEG-LMWH/PEG-HBP hydrogels were conducted at 25 or 37° C. on a stress-controlled rheometer (MCR 500, Paar Physica, Anton-Paar, Ashland, Va.) with a 25.0 mm diameter parallel plate geometry and a 1 mm gap distance. Strain sweeps were performed on samples from 0.001% to a maximum strain of 100% to determine the limit of the linear viscoelastic regime (LVE). At a constant strain of 0.1%, chosen from the LVE, frequency sweeps ranging from 0.1 Hz to 100 Hz were conducted. Shear recovery experiments were also performed for the PEG-$PF_4ZIP$-containing hydrogels, and prior to these experiments, a baseline oscillation at a constant strain of 0.1% and a constant frequency of 10 Hz was performed, followed by a high-speed rotation with a 1000 s−1 shear rate for 10 s. The recovery was then measured with a time sweep experiment at a constant strain of 0.1% and a constant frequency of 10 Hz.
Fluorimetry Experiments Fluorimetry experiments to measure the concentration of PEG-LMWH-Alexa Fluor 350 (in eroded solutions of PEG-$PF_4ZIP$-containing hydrogels) were performed using a FluoroMax-3 spectrofluorometer (Jobin Yvon Inc, Edison, N.J.) with a xenon arc lamp illuminator. Erosion of PEG-LMWH from other PEG-HBP-containing hydrogels was determined gravimetrically. 45 µL of each sample were loaded into a cuvette and excited at 346 nm, the excitation spectra peak value of Alexa Fluor 350. The emission spectra peak value at 442 nm was recorded. Solutions of PEG-LMWH-Alexa Fluor 350 in PBS, with concentrations from 5.42×10-4 wt % to 4.23×10-6 wt %, were employed for generation of the standard curve. For erosion profile experiments, the PEG- LMWH-Alexa Fluor 350 was premixed with the PEG-LMWH at a weight ratio of 1:158. The fluorescence intensities of the PEG-LMWH-Alexa Fluor 350 in the eroded PEG-LMWH were then measured and permitted calculation of the percentage of PEG-LMWH eroded from the hydrogels in hydrogel erosion experiments.

Assembly of PEG-LMWH/PEG-HBP (and PEG-LMWH/GF) Hydrogels

The PEG-LMWH/PEG-HBP hydrogels were formed by the interaction between LMWH and PF4ZIP. 5 wt % solutions of the PEG-HBP in PBS were added directly to 2.5 wt % solutions of the PEG-LMWH in PBS, to afford hydrogel networks at a final composition of 2.5 wt % total polymer. The solutions were mixed in ligand mole ratios of 9:0.5, 8:1, and 7.5:2.5 (LMWH:PF$_4$ZIP dimer); other ligand mole ratios are also useful for hydrogel assembly. For VEGF-crosslinked hydrogels, an 8 wt % solution of PEG-LMWH in PBS is mixed with varying amounts of solid VEGF (0.1-20 μg) to afford a self-supporting gel upon sufficient addition of VEGF. After mixing, the hydrogels were stored at 4° C. The stored hydrogels were equilibrated to room temperature prior to rheological characterization (typically several minutes).

bFGF Release and Hydrogel Erosion Experiments bFGF release and hydrogel erosion experiments were performed at 4° C. in 24-well polystyrene assay plates (Corning Inc., Corning, N.Y.), blocked with PBS containing 5% BSA and 0.05% Tween 20 (Sigma, St. Louis, Mo.). The wells were aspirated and washed 4 times with 0.05% Tween 20 in PBS before loading samples. Afterward, 200 μL hydrogel was placed on the bottom of each well and 2.8 mL PBS was added carefully over each gel. 1 mL PBS was taken out of the well at 1, 2, 6 and 24 h and then each following day, followed by replacement with 1 mL fresh PBS. The amount of bFGF in each sample was measured with a bFGF Quantikine kit (R&D Systems, Minneapolis, Minn.). The hydrogel erosion kinetics were conducted on the same samples used for bFGF release experiments.

Results

Oligomerization of PF$_4$ZIP

Our initial studies were aimed at determining the oligomerization properties of the coiled-coil PF$_4$ZIP, as such information is relevant to the subsequent use of the PF$_4$ZIP in hydrogel formation. No such characterization was necessary for the other HBPs, as they do not form higher-order assemblies. Circular dichroic spectroscopy studies were conducted to assess the folding of the PF$_4$ZIP under various conditions. Solutions of PF$_4$ZIP dissolved in PBS were scanned from 250 nm to 200 nm at varying temperatures between 5° C. and 75° C. The CD spectra of PF$_4$ZIP at a variety of temperatures show an isodichroic point at 203 nm, validating the existence of a two-state equilibrium. At temperatures below 55° C., the spectra observed exhibit two minima at 208 nm and 222 nm, demonstrating that PF$_4$ZIP exists in the coiled-coil state under conditions of interest for hydrogel applications. As seen by the appearance of a single minimum at 203 nm in the data collected at elevated temperatures, the structure of PF$_4$ZIP reversibly changes to random coil at elevated temperature. Maximum mean residue ellipticity values at 222 nm (MRE222) were measured to be −30,470 deg cm$^2$ dmol$^{-1}$ for the PF$_4$ZIP at 15° C., consistent with reported values ranging from −25,000 to −35,000 deg cm$^2$ dmol$^{-1}$ for various GCN$_4$-mimic peptides in PBS at 15° C.

Figure 17:
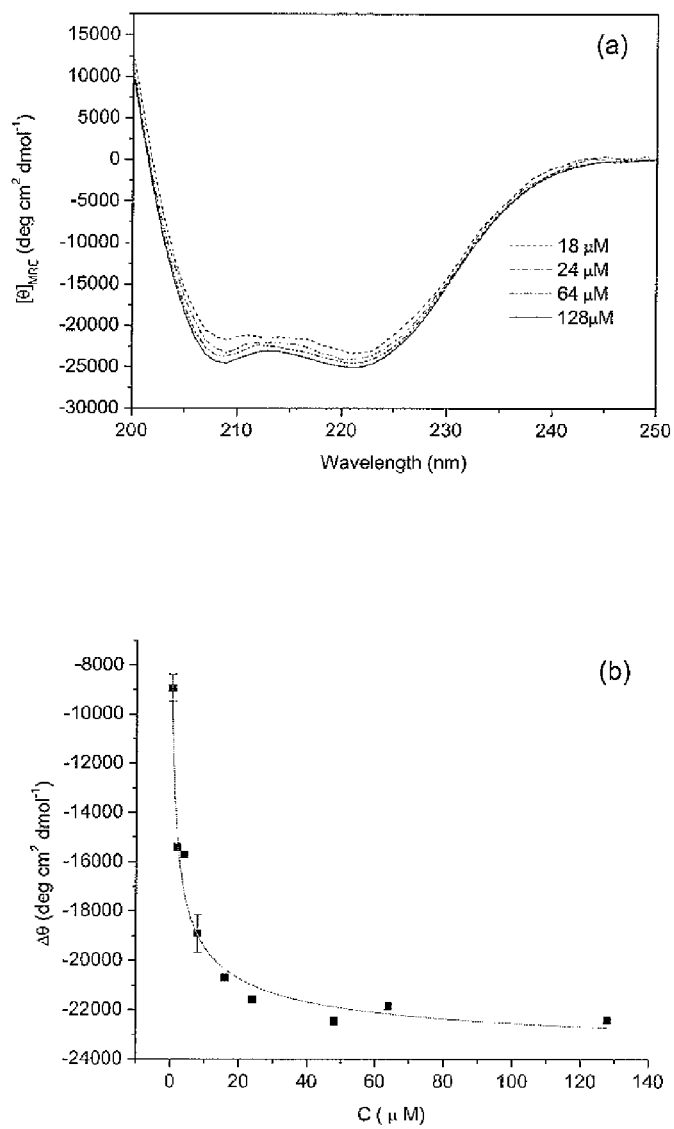
FIG. 17 shows (a) CD spectra of PEG-PF4ZIP at different concentrations in PBS at 25° C.; (b) Concentration dependence of the MRE for PEG-PF4ZIP at 222 nm. The solid line is the best fit.

The conformation of PF$_4$ZIP at various concentrations was also monitored via CD. At all measured concentrations, the spectra observed exhibit two minima at 208 nm and 222 nm, demonstrating the helical character of PF$_4$ZIP under these conditions. The measured MRE222 for a solution of 56 μM PF$_4$ZIP in PBS is −24,580 deg cm$^2$ dmol$^{-1}$, which is consistent with the value reported for 40~60 μM PF$_4$ZIP in 3 mM sodium citrate buffer (−27,000 deg cm$^2$ dmol$^{-1}$). The difference between the measured ellipticity and the ellipticity of the unfolded monomer is related to concentration and can be fit to determine the Kd of the dimerization, via standard fitting procedures well-described in the literature. The calculated equilibrium constant of unfolding, Kd, is 3.48±0.03 μM. Solutions of PF$_4$ZIP attached to star-PEG were also studied via CD, to ensure that conjugation to PEG did not significantly alter the association of the PF$_4$ZIP coiled-coils. As shown in FIG. 17($a$), the spectra of PEG-PF$_4$ZIP are essentially identical to the spectra obtained for the isolated PF$_4$ZIP. Slight differences in MRE values likely arise from uncertainties in the precise peptide concentrations for the PEG-PF$_4$ZIP samples. The Kd value derived from the best fit of the concentration dependence of (FIG. 17($b$)) for PEG-PF$_4$ZIP is 0.93 μM. The PF$_4$ZIP concentrations during NMR characterization and hydrogel formation and characterization are always much greater than these measured Kd values (e.g., 200 μM and higher), suggesting that PF$_4$ZIP will exist as a fully folded dimer under those conditions.

Heparin-binding Affinity

Our previous investigations of PEG-LMWH/PEG-HBP hydrogels suggested that the viscoelastic properties of the noncovalently assembled hydrogels were related to the heparin-binding kinetics and affinities of the peptides (from antithrombin III (ATIII) or heparin interacting protein (HIP)). Heparin-sepharose affinity chromatography and SPR experiments were therefore used to compare the heparin-binding affinity of the various HBPs. Results of these experiments are summarized in Table 2.

TABLE 2

Heparin binding affinity data (at 25° C.) for heparin-binding peptides determined via affinity chromatography and SPR.

| Peptide | Salt required for elution from heparin column (mM) | $k_a$ (M$^{-1}$s$^{-1}$) | $k_d$ (s$^{-1}$) | $K_D$ (μM) |
|---|---|---|---|---|
| ATIII[1] | 594 ± 2 | 1.56 ± 0.06 × 10$^2$ | 2.00 ± 0.3 × 10$^{-3}$ | 12.9 ± 1.3 |
| HIP[1] | 687 ± 1 | 1.10 ± 0.08 × 10$^3$ | 4.64 ± 0.02 × 10$^{-3}$ | 4.20 ± 0.3 |
| PF4$_{ZIP}$ | 962 ± 10 | 2.24 ± 0.05 × 10$^5$ | 2.56 ± 0.10 × 10$^{-3}$ | 1.15 ± 0.03 × 10$^{-2}$ |

The errors are derived from the average of duplicate measurements

[1]Data from previously reported studies (N. Yamaguchi, B. S. Chae, L. Zhang, K. L. Kiick, E. M. Furst, Rheological characterization of polysaccharide-poly(ethylene glycol) star copolymer hydrogels, Biomacromolecules 6 (4) (2005) 1931-1940)

For heparin affinity chromatography experiments, HBPs were loaded onto a heparin-sepharose column, and then eluted with buffer of increasing NaCl concentration. The concentration of NaCl required for peptide elution is used as an indication of the affinity of the peptide for heparin. The elution of the peptides from the heparin-sepharose column required a salt concentration of 962±10 mM for the PF$_4$ZIP peptide. The salt concentration required to elute PF$_4$ZIP (962±10 mM) is higher than that measured for the ATIII peptide (594±2 mM) and for the HIP peptide (687±1 mM), indicating that PF$_4$ZIP has higher heparin-binding affinity than the ATIII and HIP peptides and should therefore be competent for hydrogel assembly. These results are consistent with previous reports indicating that similarly high concentrations of NaCl were required to elute $^{125}$I-labelled PF$_4$ZIP bound to a heparin-sepharose column in 0.02 M Tris-HCl buffer pH 7.0 containing 0.05 M NaCl.

In SPR experiments, the interaction of the peptides with a LMWH-modified SA chip surface was determined under conditions described in the experimental section. Neither nonspecific binding of heparin-binding proteins to SA chips nor chip instability was observed in any of the SPR measurements. In addition, no mass transport limitation or linked reactions were indicated. The measured association of the PF$_4$ZIP with LMWH proceeds with a rate constant of 2.24±0.05×10$^5$ M$^{-1}$ s$^{-1}$, while the dissociation proceeds with a rate constant of 2.56±0.10×10$^{-3}$ s$^{-1}$, yielding a KD of approximately 1.15±0.03×10$^{-2}$ μM. These faster association kinetics, relative to those reported for the ATIII and HIP (Table 2) (see also N. Yamaguchi, B. S. Chae, L. Zhang, K. L. Kiick, E. M. Furst, *Rheological characterization of polysaccharide-poly (ethylene glycol) star copolymer hydrogels*, Biomacromolecules 6 (4) (2005) 1931-1940) are the primary cause of the lower measured KD values for PF$_4$ZIP-LMWH binding, and the trend of the dissociation constants is consistent with the chromatography results. The more rapid association rate, coupled with the similar dissociation rate, of PF$_4$ZIP versus the other HBPs, points to the successful formation of hydrogels between PEG-PF$_4$ZIP and PEG-LMWH. The measured K$_D$ of the binding between PF$_4$ZIP and LMWH is lower than the measured Kd of dissociation of the coiled-coil obtained from CD experiments, which may suggest that the LMWH-functionalized surface facilitates coiled-coil formation. Nevertheless, the equilibrium constants of dissociation determined via both methods are substantially lower than the concentrations employed during hydrogel formation experiments (see below).

Temperature Dependence of PF$_4$ZIP Binding

The heparin-binding kinetics between LMWH and PF$_4$ZIP were monitored via SPR at several temperatures between 5° C. and 37° C., to determine potential changes in binding kinetics that might alter hydrogel properties under physiological conditions. Data from these experiments are shown in Table 3.

TABLE 3

Heparin-binding affinity data for PF4$_{ZIP}$ at different temperatures, as determined via SPR.

| Temperature (° C.) | k$_a$ (M$^{-1}$s$^{-1}$) | k$_d$ (s$^{-1}$) | K$_D$ (μM) |
|---|---|---|---|
| 5 | 1.56 ± 0.01 × 10$^5$ | 3.74 ± 0.17 × 10$^{-3}$ | 2.41 ± 0.10 × 10$^{-8}$ |
| 15 | 1.90 ± 0.04 × 10$^5$ | 1.67 ± 0.03 × 10$^{-3}$ | 8.82 ± 0.02 × 10$^{-9}$ |
| 25 | 2.24 ± 0.05 × 10$^5$ | 2.56 ± 0.10 × 10$^{-3}$ | 1.15 ± 0.03 × 10$^{-8}$ |
| 37 | 5.11 ± 0.02 × 10$^5$ | 2.44 ± 0.08 × 10$^{-3}$ | 4.78 ± 0.14 × 10$^{-9}$ |

The errors are derived from the average of duplicate measurements

The measured on and off rates fluctuate only slightly throughout the temperature range, suggesting that noncovalently assembled hydrogels based on PF$_4$ZIP and LMWH interactions should exhibit consistent mechanical properties at these temperatures.

PEG-LMWH/PEG-HBP Hydrogel Formation

Via $^1$H NMR spectroscopy, functionalization of the star PEG with HBPs was determined to be at least 59%, indicating that PEG-HBPs meet the functional requirement (at least one binding partner exhibits f>2) for crosslinking a hydrogel upon interaction with PEG-LMWH (which showed a functionalization of 81%, as determined via NMR). (see N. Yamaguchi, K. L. Kiick, *Polysaccharide-poly (ethylene glycol) star copolymers as scaffolds for the production of bioactive hydrogels*, Biomacromolecules 6 (4) (2005) 1921-1930; and N. Yamaguchi, B. S. Chae, L. Zhang, K. L. Kiick, E. M. Furst, *Rheological characterization of polysaccharide-poly (ethylene glycol) star copolymer hydrogels*, Biomacromolecules 6 (4) (2005) 1931-1940).

Figure 18:
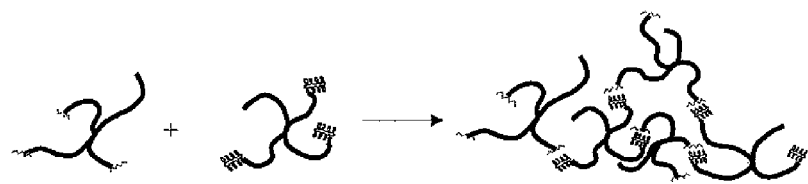
FIG. 18 is a schematic of the assembly of hydrogels from solutions of the two polymer conjugates. The PF4ZIP is rendered as an oligomerized coiled-coil, as its concentration (200 µM) under these experimental conditions is two orders of magnitude greater than the measured Kd value.

Accordingly, solutions of the two polymer conjugates in PBS (2.5 wt % of the PEG-LMWH and 5 wt % of the PEG-HBP) were mixed at various ligand molar ratios to form hydrogels. Ligand molar ratios of 9:0.5 and 7.5:2.5 (LMWH:PF$_4$ZIP) were used to yield the PEG-LMWH/PEG-PF4ZIP hydrogels. Similar ratios were used for the formation of functionalized crosslinked matrices from mixtures of PEG-LMWH with either PEG-ATIII or PEG-HIP, and any PEG-HBP conjugate should be useful in a similar manner. The application of such ratios was employed to maximize the excess LMWH available for growth factor binding (see below). Before addition of PEG-PF$_4$ZIP, the 2.5 wt % of the PEG-LMWH was uniform and translucent. In addition, the water-like viscosity of the PEG-PF$_4$ZIP solution indicated that there was no significant crosslinking of the peptide-terminated star polymers via intermolecular coiled-coil formation, although some oligomers of the PEG-PF$_4$ZIP bioconjugates may exist in solution. The formation of self-supporting, opaque gels was immediately apparent upon mixing the two polymer solutions. A schematic of the assembly of the hydrogels is shown in FIG. 18. This assembly is operative regardless of the identity of the PEG-HBP.

Bulk Rheology

Figure 19:
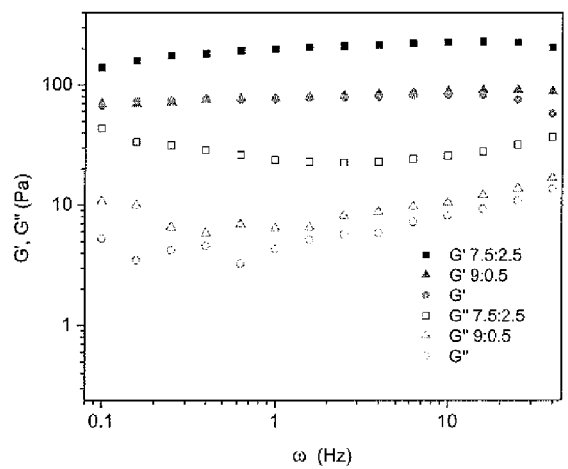
FIG. 19 depicts storage moduli (closed symbols) and loss moduli (open symbols) of the PEG-LMWH/PEG-PF4ZIP hydrogels for different molar ratios. The response of 2.5 wt % of the PEG-LMWH (circles) is shown for comparison.

The mechanical properties of the PEG-HBP containing hydrogels were characterized via rheological frequency sweep experiments on bulk samples. The frequency sweep results for PEG-LMWH/PEG-PF$_4$ZIP hydrogels (FIG. 19) show that the storage modulus G'(ω) is significantly larger than the loss modulus G"(ω) over all measured frequencies and G'(ω) exhibits a pronounced plateau extending to frequencies of tens of reciprocal seconds, indicating a viscoelastic gel. Essentially identical results are obtained regardless of the identity of the PEG-HBP. The magnitude of G'(ω) and G"(ω) also increases as the molar ratio of the peptide component is raised. The average G'(ω) increases from an average value of 70 Pa for PEG-LMWH to approximately 80 and 180 Pa for hydrogels with molar ratios of LMWH to PF4ZIP of 9:0.5 and 7.5:2.5, respectively. The average G"(ω) also increases monotonically with higher molar ratio of the peptide component, from less than 10 Pa for PEG-LMWH to more than 30 Pa for hydrogels with molar ratios of LMWH to PF4ZIP of 7.5:2.5. Bulk rheology experiments were also performed on the samples at various gap heights of 1 mm, 0.5 mm, and 0.25 mm. At frequencies from 0.1 to 63 Hz, the observed identical dynamic moduli at different gap heights indicate that no significant slipping occurs in that frequency range.

Figure 20:
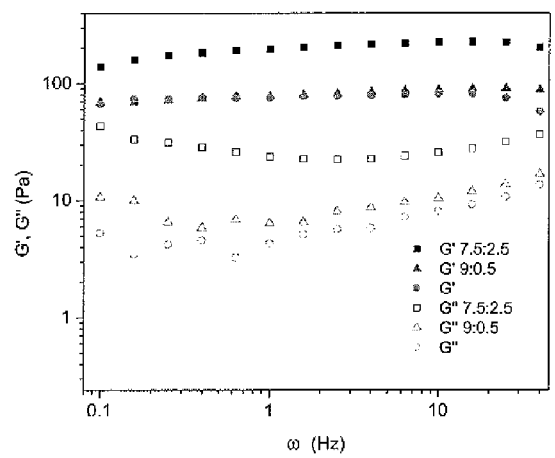
FIG. 20 shows plots of normalized storage moduli G' (ω=0.1 Hz) as a function of HBP (PF4ZIP, ATIII or HIP) to LMWH. HIP and ATIII data are adapted from reference 12.

The strengthening effects on storage modulus upon addition of PEG-HBP to PEG-LMWH are presented in FIG. 20 for G' (ω=0.1 Hz) plotted as a function of the ratio of HBP to LMWH in the samples, with moduli normalized by the initial storage modulus of PEG-LMWH. The plateau in the modulus with increasing PF$_4$ZIP or HIP concentration may imply that the HBP-binding sites on LMWH have been saturated. The increase in the elastic modulus upon addition of PEG-PF$_4$ZIP for the PEG-LMWH/PEG-PF$_4$ZIP hydrogels is lower than that observed with addition of PEG-HBP for the PEG-LMWH/PEG-ATIII or the PEG-LMWH/PEG-HIP hydrogels. Literature reports suggest that at least 4 tetrasaccharides (16 units) are required for efficient heparin-PF4 protein interactions, while HIP- and ATIII-binding sites are believed to be similar pentasaccharides in heparin. The fewer PF$_4$-binding sites on LMWH could lead to the lower storage modulus plateau value and lower slope in FIG. 20 for the PEG-LMWH/PEG-PF$_4$ZIP hydrogels than that observed for the PEG-LMWH/PEG-ATIII or the PEG-LMWH/PEG-HIP hydrogels. These results indicate two things. First, the mechanical properties of the hydrogels are initially established by the self-interaction/assembly of PEG-LMWH. Second, the dependence of storage modulus on HBP:LMWH ratio clearly indicates that the PEG-HBPs mediate crosslinking of the networks and that the interactions between HBP and LMWH modulate the mechanical properties of the matrices.

A similar dependence of rheological properties on the concentration of heparin-binding cross-linker was observed for PEG-LMWH crosslinked with VEGF. Laser tweezer microrheology experiments, in this case, confirmed the elastic behavior of the hydrogels at low and moderate frequencies, and also demonstrated that the development of elastic properties of the network are dependent on the concentration of VEGF present in the network. Microrheology characterization was conducted on 4 wt % hydrogels in order to reduce the elastic modulus sufficiently for measurement. 8 wt % hydrogels provide improved mechanical properties, although a variety of concentrations could be used depending on the desired application.

The rheological properties of the PEG-LMWH/PEG-PF$_4$ZIP hydrogels were also investigated at physiological temperature. The mechanical properties of the hydrogels with molar ratios of LMWH to PF$_4$ZIP of 9:0.5 and 7.5:2.5 were examined. The frequency sweep data for the hydrogel (LMWH:PF4ZIP=9:0.5) are presented in FIG. 21. The moduli at 25° C. or 37° C. are essentially identical, with an identical frequency dependence, although the gels at 37° C. exhibit slightly lower loss moduli at higher frequencies. The materials are therefore also elastic hydrogels at 37° C., in corroboration of the SPR studies. This lack of temperature dependence is also observed in the hydrogel with higher PF$_4$ZIP content, reflecting the temperature insensitivity of both the PF$_4$-LMWH interactions and the LMWH-LMWH interactions.

Figure 21:
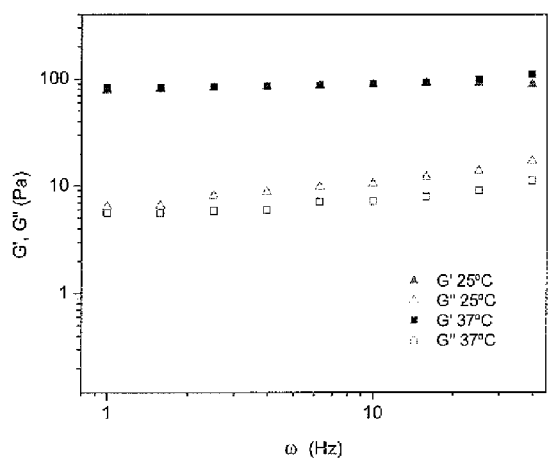
FIG. 21 is a comparison of storage moduli (closed symbols) and loss moduli (open symbols) of the PEG-LMWH/PEG-PF4ZIP hydrogels (LMWH:PF4ZIP-9:0.5) obtained 25° C. and 37° C.
Figure 22:
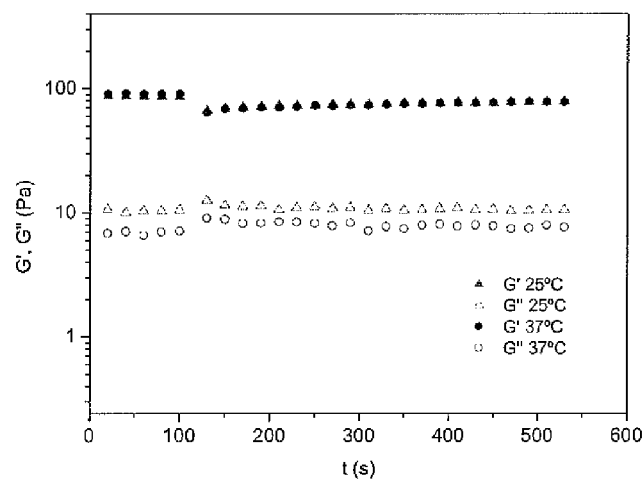
FIG. 22 shows shear recovery data for PEG-LMWH/PEG-PF4ZIP hydrogels (LMWH:PF4ZIP=9:0.5) at 25° C. and 37° C.

Shear recovery data for the PEG-LMWH/PEG-PF$_4$ZIP hydrogels are exhibited in FIG. 22. Both the extent and time-dependence of recovery were determined in these experiments. FIG. 22 indicates that after the hydrogels are subjected to a steady shear rate as high as 1000 s$^{-1}$, they essentially immediately recover their elastic properties, so only a slight reduction in modulus can be measured. In addition, the moduli at 25° C. and 37° C. are equal, with a matching kinetics of recovery. The data are consistent with previous rheological frequency sweep studies (FIG. 21). The immediate recovery and stability of the PEG-LMWH/PEG-PF4ZIP hydrogels even after subjected to high shear suggests their potential utility in injectable applications.

Growth Factor Release and Hydrogel Erosion

The release of growth factors from these hydrogels in vitro has also been investigated. Although covalently crosslinked, heparin-containing hydrogels have been shown to be useful for release of bFGF, physically crosslinked hydrogels could provide an alternative protein-delivery matrix without the need for potentially toxic crosslinking reagents.

The bFGF release and hydrogel erosion experiments were performed at 4° C. in 24-well polystyrene assay plates. A 2.5 wt % solution of PEG-LMWH with bFGF was prepared via dissolving PEG-LMWH and bFGF in PBS at a final molar ratio of approximately 1:1,500,000 (bFGF to LMWH). Secondly, a 5 wt % solution of PEG-PF$_4$ZIP (or other PEG-HBP) in PBS was added to the PEG-LMWH/bFGF at a ligand molar ratio of 8:1 (LMWH:PF4ZIP dimer). Other molar ratios can also be used, depending upon the desired rate of release of the growth factor and/or desired rate of erosion of the network. Assuming that all HBPs on the PEG-HBP termini bind LMWH, the molar ratio of bFGF to available LMWH in the PEG-LMWH/PEG-HBP hydrogels is approximately 1:1,300,000.

Figure 23:
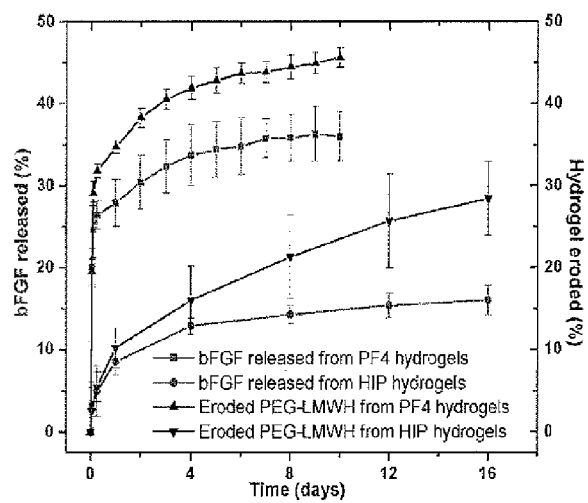
FIG. 23 depicts the bFGF release and hydrogel erosion profiles of the PEG-LWMH/PEG-PF4ZIP hydrogel (LMWH:PF4ZIP=8:1) and the PEG-LMWH/PEG-HIP hydrogel (LMWH:HIP 8:2). The errors are derived from the average of at least duplicate measurements.

Data from studies of bFGF release from PEG-LMWH/PEG-HIP and PEG-LMWH/PEG-PF$_4$ZIP hydrogels are summarized in FIG. 23. As shown in the figure, a burst release of bFGF ranging from 10 to 25% (depending on gel identity) is observed, followed by a slow release of bFGF over 10 days, to a maximum measured release ranging from approximately 20 to 35%. Such release profiles are of potential use in neovascularization, wound repair, and tissue engineering applications. As shown in FIG. 23, the bFGF is released slightly more quickly from the PEG-LMWH/PEG-PF$_4$ZIP hydrogels than from the PEG-LMWH/PEG-HIP hydrogels, indicating that the rates of release of growth factor from these hydrogels are tunable based on hydrogel composition. The PEG-LMWH/PEG-HIP hydrogel demonstrates higher storage and loss moduli than the PEG-LMWH/PEG-PF$_4$ZIP hydrogels. The observed burst release is similar in value to previously reported burst release in other heparinized hydrogel system, and the linear release following the initial burst in those hydrogel systems has been successfully applied to stimulate cell proliferation.

Hydrogel erosion kinetics are also shown in FIG. 23. In the case of the PEG-LMWH/PEG-PF$_4$ZIP hydrogels, PEG-LMWH-Alexa Fluor 350 was pre-mixed with PEG-LMWH at a weight ratio of 1:158 to facilitate tracking of the eroded PEG-LMWH via fluorimetry. The erosion profile of the PEG-LMWH/PEG-HIP hydrogels was determined gravimetrically in the transwell assay format in conjunction with the bFGF release experiments. As shown in the figure, a burst erosion of 10 to 30% is initially observed (depending on hydrogel composition), followed by a slow erosion to a maximum of 30 to 50% (again, depending on hydrogel composition). As is also indicated in this figure, the growth factor release is directly correlated to the erosion of the hydrogel, and can therefore be controlled by modulating hydrogel mechanical properties. Modulating the affinity of the growth factor to the hydrogel will also serve as an additional strategy to control release rates.

Growth factors released from hydrogels of these general compositions have also been shown to be bioactive, indicating the utility of these matrices in desired applications. For example, bFGF released from PEG-LMWH functionalized hydrogels (covalently crosslinked model systems) (procedure for covalent crosslinking is provided in N. Yamaguchi, K. L. Kiick, *Polysaccharide-poly (ethylene glycol) star copolymers as scaffolds for the production of bioactive hydrogels*, Biomacromolecules 6 (4) (2005) 1921-1930, which is incorporated herein by reference) has been shown, via MTT (3-(4,5-Dimethylthiazol-2-yl)-2,5-diphenyltetrazolium bromide) proliferation assays, to increase proliferation of HUVECs (human umbilical vein endothelial cells) in a bFGF-dose-responsive manner. In these assays, the amount of yellow MTT oxidized to purple formazan is measured spectrophotometrically as a function of the amount of bFGF loaded in the hydrogel. Average increases in formazan salt formation ranged from 1.5 to 4 fold in the bFGF proliferation experiments. In another set of experiments, VEGF released from the PEG-LMWH/VEGF hydrogels has been shown to increase the rate of proliferation of porcine aortic endothelial (PAE) cells in DMEM media. Assays were conducted in a transwell assay format as described in N. Yamaguchi, K. L. Kiick, *Polysaccharide-poly (ethylene glycol) star copolymers as scaffolds for the production of bioactive hydrogels*, Biomacromolecules 6 (4) (2005) 1921-1930. Measured increases in the proliferation rate, assessed via cytometry, have ranged from 25-50%. These results complement and are similar to the results obtained in Example 3, which indicate the bioactivity of growth factor-loaded electrospun matrices. Similar bioactivity of any growth factor sequestered in these matrices is expected, based on these results, and on the general observation of growth factor activity preservation in heparinized matrices.

Example 5

Cell-Mediated Delivery and Targeted Erosion of VEGF-Cross-Linked Hydrogels

To test the potential of these hydrogels to selectively release VEGF (and thus erode) in response to cells that overexpress VEGFR-2, two engineered endothelial cell types were employed. [PEG-LMWH/VEGF] was incubated in the presence of porcine aortic endothelial cells (PAECs) engineered to overexpress ($2.5 \times 10^5$ VEGFR-2 per cell; PAE/KDR) or in the presence of cells lacking the transcript for VEGFR-2 (PAE). The cumulative release of VEGF and PEG-LMWH were monitored in a transwell assay cell culture format in which hydrogels were placed in the transwell insert and PAECs were cultured on the PS surface of the well of a 24-well plate. A well lacking any cells was employed as a control. This transwell assay format optimized cell proliferation and was necessary given that the hydrogels lack any cell-adhesive domains; this format is also representative of situations in which the [PEG-LMWH/VEGF] would be employed as a drug delivery vehicle. The two types of PAE cells were also used to evaluate the impact, on endothelial cell proliferation, of the released VEGF from the non-covalently assembled [PEG-LMWH/VEGF]. The phosphorylation of VEGFR-2 was also investigated in the presence and absence of the VEGF-containing hydrogel to determine whether the release of the VEGF activated the target receptor.

Release of PEG-LMWH

Figure 24:
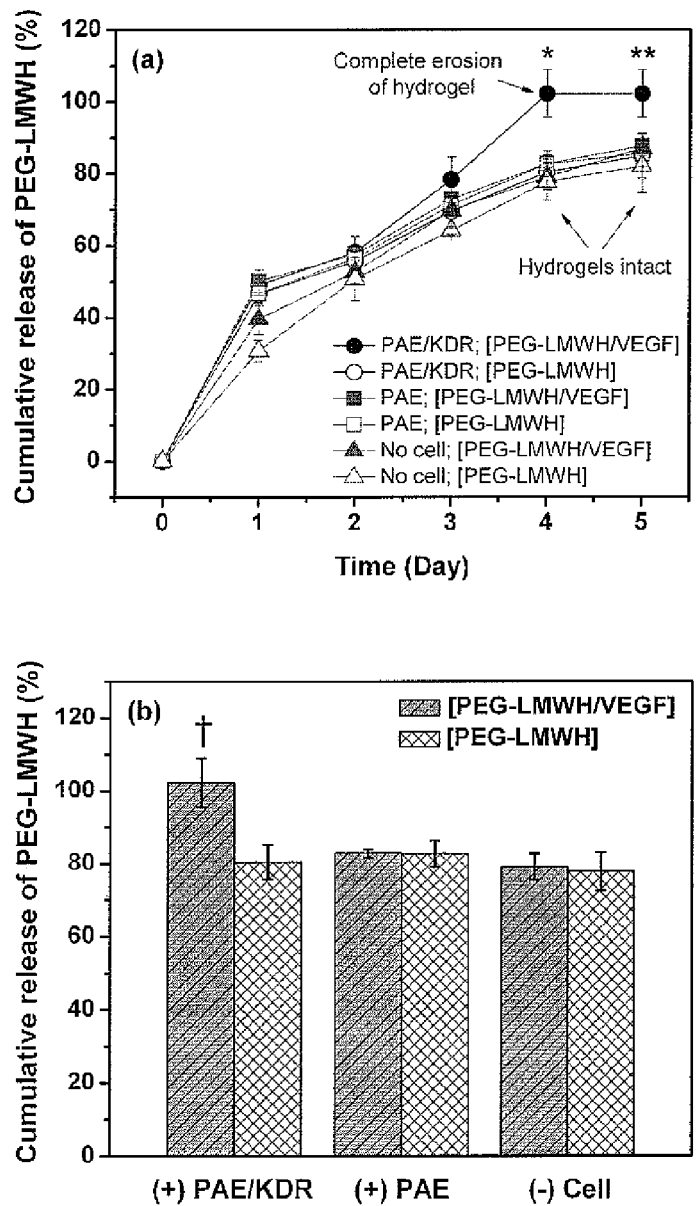
FIG. 24 shows the release of PEG-LMWH from non-covalently assembled hydrogels as indicative of hydrogel erosion. (a) The release profiles of [PEG-LMWH/VEGF] (closed) or [PEG-LMWH] (open) hydrogels, in the presence of PAE/KDR (•; ○) and PAE (■; □) or in the absence of cells (▲; △), respectively. *p<0.001; **p<0.007. (b) The cumulative release of PEG-LMWH at day 4. †p<0.001.

The impact of VEGFR-2, the main mitogenic VEGF receptor, on hydrogel erosion was investigated by monitoring the release of the PEG-LMWH carrier from the gels in the presence of PAE cells equipped with or without the VEGFR-2, i.e. PAE/KDR or PAE, respectively. PAE/KDR or PAE were seeded in 24-well plates for each data point (1, 2, 3, 4, and 5 days; data were not collected after day 5 owing to the confluence of the PAECs.). The [PEG-LMWH/VEGF] or [PEG-LMWH] hydrogels were placed on a transwell support and these were inserted in each of the cell-containing wells, respectively. The amount of PEG-LMWH in the removed aliquots of medium was evaluated via toluidine blue assay. The cumulative release of PEG-LMWH from hydrogels is shown in FIG. 24, and indicates the degree of hydrogel erosion. Specifically, FIG. 24(a) shows the release profiles of PEG-LMWH from the [PEG-LMWH/VEGF] and [PEG-LMWH] in the presence of PAE/KDR, PAE cells and in the absence of cells. Burst release was observed in all sets of gels, with 49.0±2.8% release of PEG-LMWH from [PEG-LMWH/VEGF] in the presence of PAE/KDR and an average of 43.6±6.8% release in other samples. The cumulative release of PEG-LMWH at day 4 under all different experimental conditions is shown in FIG. 24(b) to facilitate comparison.

The release profiles of PEG-LMWH in all samples were similar during this experiment, except for that of [PEG-LMWH/VEGF] in the presence of PAE/KDR; this exception was statistically significant from day 3 onward ($p<0.001$ at day 4 and $p<0.007$ day 5), with an approximate 20% difference in release between the samples after day 4. The [PEG-LMWH/VEGF] hydrogel was completely eroded by day 4 in the presence of PAE/KDR, whereas the hydrogels in all other samples remained intact until the end of the release experiment (day 5). Comparison of PEG-LMWH release from [PEG-LMWH/VEGF] versus [PEG-LMWH] hydrogels in the presence of PAE/KDR indicated the greater rate of erosion of the VEGF-crosslinked hydrogel (FIG. 24(b) ($p<0.001$)), confirming that the binding of VEGF to VEGFR-2 accelerates the erosion of [PEG-LMWH/VEGF]. The fact that the release of PEG-LMWH for all other samples is essentially identical confirms not only that both VEGF and VEGFR-2 are necessary for the accelerated erosion and but also that other cell-surface molecules of the PAECs do not accelerate erosion of these gels. Otherwise, the release of PEG-LMWH from the gels in the presence of PAE would be greater than that observed in the absence of cells. In addition, given the similarity in release profiles of the [PEG-LMWH] gels in the presence and absence of PAE cells, erosion of [PEG-LMWH] is suggested to occur via passive diffusion. This result clearly indicates that the presence of VEGFR-2 on cell surfaces accelerates the erosion of [PEG-LMWH/VEGF] hydrogels.

Release of VEGF

Figure 25:
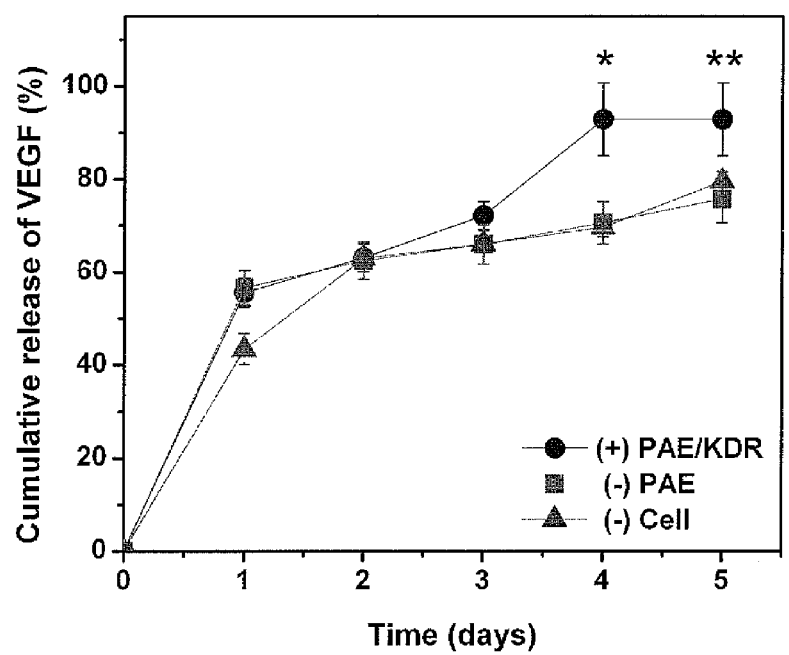
FIG. 25 shows the release profile of VEGF from non-covalently assembled [PEG-LMWH/VEGF] hydrogel. Release profiles of VEGF in the presence of PAE/KDR (•) or PAE (■) cells, and in the absence of cell (▲), respectively. *P<0.002; **p<0.004.

Release of VEGF in response to the VEGFR-2 presenting cells was also investigated for comparison with PEG-LMWH release. The release of VEGF from [PEG-LMWH/VEGF] hydrogels in the presence and absence of cells was monitored by measuring the radioactivity of $^{125}$I-labeled VEGF in the collected medium. The release profiles are shown in FIG. 25. In general, the release profiles of VEGF exhibited very similar trends to those observed for PEG-LMWH release from [PEG-LMWH/VEGF] hydrogels. The VEGF release in the presence of PAE/KDR showed a burst release of 55.6±3.0% at day 1, and reached a maximum of 92.9±7.8% at day 4. In contrast, burst release of 56.7±3.8% was observed at day 1 in the presence of PAE, and the cumulative release was 75.7±5.1% at day 5. The initial release of VEGF from [PEG-LMWH/VEGF] hydrogels in the absence of cells was 43.4±3.4% with a cumulative release of 79.6±2.0% at day 5. VEGF release from [PEG-LMWH/VEGF] reached the maximum at day 4 in the presence of PAE/KDR, concurrent with the complete erosion of the gel.

Figure 26:
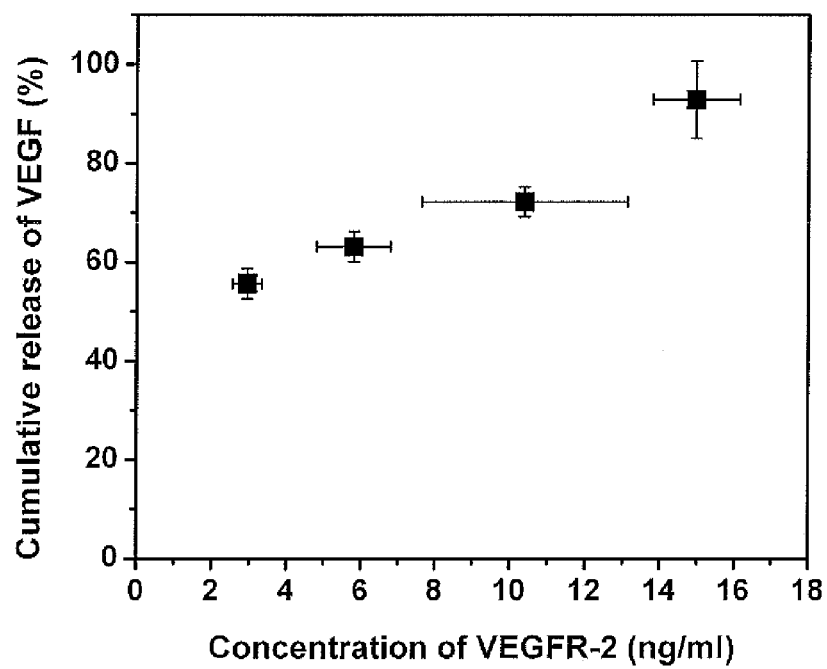
FIG. 26 shows the release of VEGF with respect to the concentration of VEGFR-2 in PAE/KDR cell cultures.

That the release of VEGF from the [PEG-LMWH/VEGF] was in fact mediated by VEGFR-2, rather than by other select surface molecules present on PAE/KDR, was also confirmed by the correlation of the amount of liberated VEGF with the concentration of the VEGFR-2 present in the PAE/KDR cultures, as determined by immunochemical methods. The concentration of VEGFR-2 from the PAE/KDR cells in the presence of the [PEG-LMWH/VEGF] was measured daily using an ELISA kit for total VEGFR-2. The cumulative release of VEGF is graphically presented versus the measured concentration of VEGFR-2 in FIG. 26. The data presented in FIG. 26 clearly indicate the correlation of the release of VEGF from [PEG-LMWH/VEGF] with the total amount of VEGFR-2 present on PAE/KDR, indicating that the VEGF release and consequent [PEG-LMWH/VEGF] erosion was accelerated due to the demand for VEGF by VEGFR-2. These results suggest that non-covalently assembled [PEG-LMWH] hydrogels provide a viable strategy for targeted hydrogel erosion and drug delivery for any therapeutic compound capable of non-covalent binding to heparin, for example, growth factors and growth factor agonists and antagonists.

Phosphorylation of VEGFR-2

Figure 27:
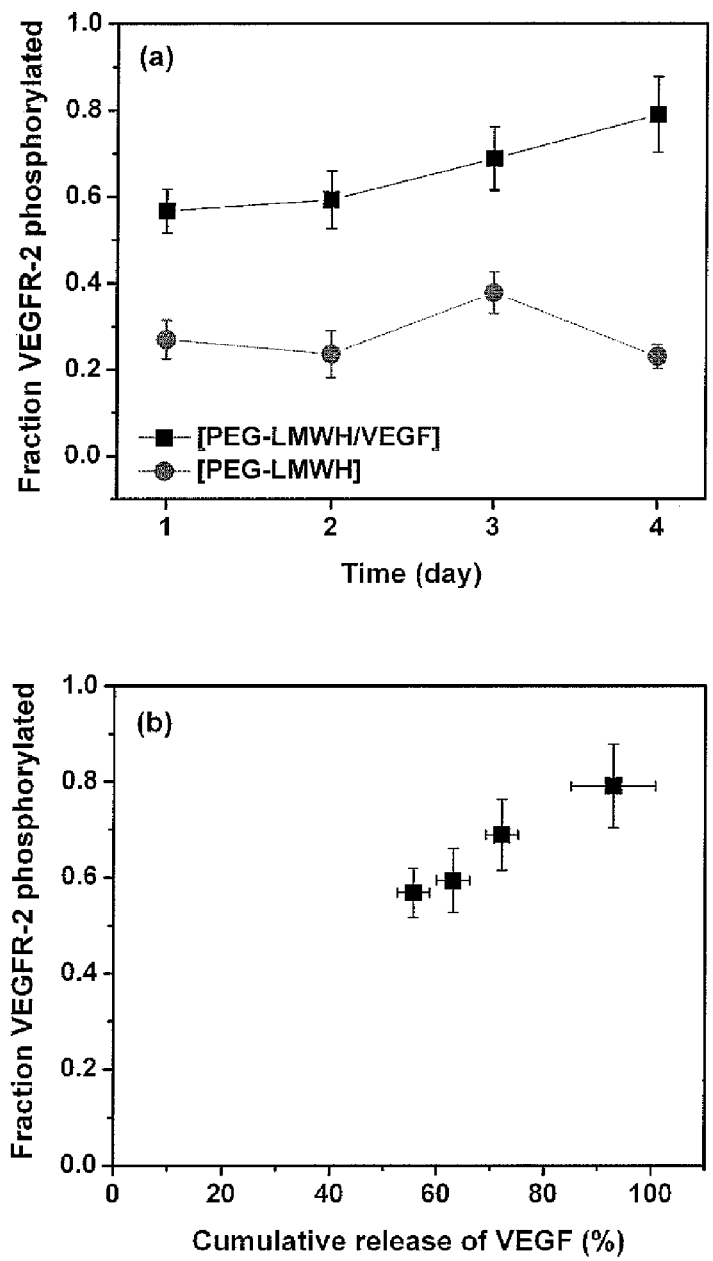
FIG. 27 shows the phosphorylated fraction of VEGFR-2 in PAE/KDR cultures. (a) Phosphorylation of VEGFR-2 of PAE/KDR cultured in the presence of [PEG-LMWH/VEGF] (■) and [PEG-LMWH] (•) hydrogels. (b) Phosphorylation of VEGFR-2 as a function of cumulative release of VEGF from the [PEG-LMWH/VEGF] hydrogel.

The effect of released VEGF, from the [PEG-LMWH/VEGF] hydrogel, on the activation of VEGFR-2 was monitored via assessment of the degree of tyrosine phosphorylation of VEGFR-2 observed in response to released VEGF. Upon binding with VEGF, the VEGFR-2 undergoes dimerization and tyrosine phosphorylation, resulting in mitogenic, chemotactic, and prosurvival signals. The efficacy of delivered VEGF, and the responsiveness of the endothelial cells to the gels, can therefore be indicated by the level of VEGFR-2 phosphorylation, which was determined immunochemically. FIG. 27 presents the fraction of phosphorylated VEGFR-2 (relative to the total VEGFR-2 isolated from PAE/KDR cells), as a function of time. The cells were lysed at each data point in the presence of kinase inhibitors to maintain the level of phosphorylation at the time of cell collection. The concentration of total VEGFR-2 and concentration of phosphorylated VEGFR-2 in lysates were measured using ELISA kits. As shown in the data, the phosphorylated fraction of VEGFR-2 in PAE/KDR cultures incubated with the VEGF-releasing hydrogel [PEG-LMWH/VEGF] increased from 0.57±0.05 at day 1 to 0.79±0.09 ($p<0.003$) at day 4. This level was significantly higher than that observed in control experiments in which PAE/KDR were cultured in the presence of the [PEG-LMWH] hydrogel (0.28±0.07, FIG. 27($a$)), as well as that of a control in which cultures of PAE/KDR were incubated without hydrogel (0.22±0.04, not shown); in addition, the level of phosphorylation in the control did not show a clear increase with time.

The fraction of phosphorylated VEGFR-2 was plotted against the cumulative release of VEGF from the [PEG-LMWH/VEGF] hydrogels, to confirm that phosphorylation of the receptor was correlated with VEGF release. As shown in FIG. 27($b$), the fraction of VEGFR-2 phosphorylated was linearly correlated to the cumulative release of VEGF, confirming that the released VEGF is interacting with and stimulating the phosphorylation of VEGFR-2, and corroborating this interaction as the relevant one in modulating hydrogel behavior (release and erosion). It is also of note that although the phosphorylation of VEGFR-2 increased with released VEGF, the total VEGFR-2 expression level per cell did not change (($8.7\pm1.2)\times10^{-5}$ ng·mL$^{-1}$ per cell at day 1 vs. $(8.5\pm0.7)\times10^{-5}$ at day 4). This suggests that while the [PEG-LMWH/VEGF] hydrogels are responsive to VEGFR-2 and induce greater signaling by the cell, they do not alter VEGFR-2 expression that could present a potentially pathological response.

Proliferation of PAE Cells

Figure 28:
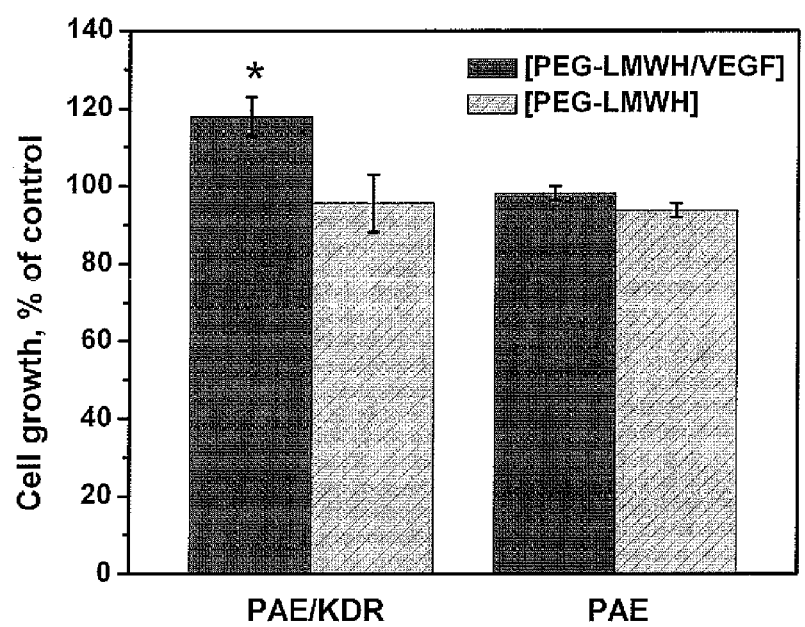
FIG. 28 depicts the proliferation of PAE/KDR and PAE cells after 4 days incubation, in the presence of non-covalently assembled [PEG-LMWH/VEGF] or [PEG-LMWH] hydrogels, respectively. The data are presented as % of control in which PAEs were cultured in the presence of 2.63 nM (100 ng/ml) VEGF in medium. *p<0.003.

The mitogenic effects of VEGF released from the hydrogels, suggested by the phosphorylation data, were corroborated in cell culture. FIG. 28 presents the percentage of cell growth (at day 4, relative to a control) of PAE/KDR and PAE in the presence of [PEG-LMWH/VEGF] and [PEG-LMWH], as colorimetrically monitored via CELLTITER-BLUE® ((Promega) reagent assay. Each cell type was cultured separately in the presence of 100 ng·mL$^{-1}$ (2.63 nM) soluble VEGF as the control. The number of cells was quantified at day 4 owing both to the complete erosion of the [PEG-LMWH/VEGF] at day 4 and the confluence of the PAE/KDR cells after day 5. As shown in the data, the PAE/KDR cultures in the presence of [PEG-LMWH/VEGF] show cell numbers approximately 120% of that observed for the control (PAE/KDR in the presence of soluble VEGF; $p<0.003$). Importantly, the number of PAE/KDR cells was Ca. 30% higher in the presence of [PEG-LMWH/VEGF] than in the presence of [PEG-LMWH] ($p<0.001$). This result is completely consistent both with the increased phosphorylation of VEGFR-2 as a result of VEGF release from [PEG-LMWH/VEGF]. In addition, the effect of [PEG-LMWH/VEGF] hydrogels on the proliferation of PAE, which lacks the VEGFR-2 transcript, was no different than the effect of the [PEG-LWMH], indicating the key role of the VEGF/VEGFR-2 interactions on the observed cell proliferation. These results indicate that VEGF released from the hydrogel is functional and selectively increases proliferation of VEGFR-2-expressing endothelial cells.

Example 6

Figure 29:
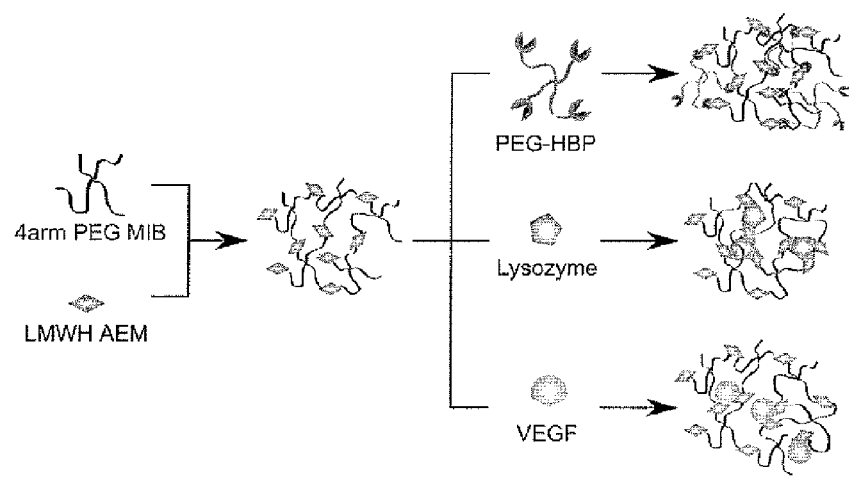
FIG. 29 shows a schematic representation of different embodiments involving covalent crosslinking of the hydrogel and non-covalent interactions between PEG-HBP, lysozyme, or VEGF and the heparinized network.

In some embodiments, erodible hydrogels are prepared via the interactions of a soluble PEG-LMWH with heparin-binding growth factors or heparin-binding peptides. In other embodiments, erodible hydrogels are prepared by the incorporation of both covalent and noncovalent crosslinking strategies. Hydrogels synthesized via such strategies are competent for formulation into bulk and nanoparticulate materials with application in tissue engineering and cell-targeted delivery FIG. 29 shows a number of embodiments involving covalently crosslinked PEG-LMWH conjugates that are further noncovalently crosslinked via interactions between PEG-HBP, lysozyme or VEGF and the heparinized network.

In one embodiment, the present invention is directed to a hydrogel comprising a polymer matrix comprising a noncovalent crosslink and a covalent crosslink, wherein the noncovalent crosslink comprises a first and a second PEG-LMWH conjugate and a heparin-binding compound, wherein the PEG molecule of each conjugate is covalently attached to the polymer matrix, and wherein the LMWH molecule of each conjugate is covalently attached to the PEG molecule of the same conjugate and noncovalently attached to the heparin-binding compound, and wherein the covalent crosslink comprises a first and a second PEG molecule and a LMWH molecule, wherein each PEG molecule is covalently attached to the polymer matrix and covalently attached to the LMWH molecule.

In another embodiment, the present invention is directed to a hydrogel comprising a polymer matrix comprising a noncovalent crosslink and a covalent crosslink, wherein the noncovalent crosslink comprises a first and a second PEG-LMWH conjugate and a first heparin-binding compound, wherein the PEG molecule of each conjugate is covalently attached to the polymer matrix, and wherein the LMWH molecule of each conjugate is covalently attached to the PEG molecule of the same conjugate and noncovalently attached to the first heparin-binding compound, and wherein the covalent crosslink comprises either (i) a third and a fourth PEG-LMWH conjugate and a second heparin-binding compound, wherein the PEG molecule of each conjugate is covalently attached to the polymer matrix, wherein the LMWH molecule of each conjugate is covalently attached to the PEG molecule of the same conjugate, and wherein the LMWH molecule of each conjugate is either covalently attached to the second heparin-binding compound or wherein the LMWH molecule of the third conjugate is covalently attached and the LMWH molecule of the fourth conjugate is noncovalently attached to the second heparin-binding compound, or (ii) a first and a second PEG molecule and a third heparin-binding compound, wherein each PEG molecule is covalently attached to the polymer matrix and covalently attached to the third heparin-binding compound.

The embodiments comprising both covalently bound and noncovalently bound heparin-binding compounds are useful for releasing these heparin-binding compounds at different times and a different rates. The noncovalently bound heparin-binding compounds may be released as provided for in Example 5 and elsewhere in the specification. For example, the noncovalently bound heparin-binding compounds may be released in burst, or relatively short time as compared to the covalently bound heparin-binding compounds. The covalently bound heparin-binding compounds may be released at a slower rate by conventional means. At least one application of the differential rate of release of the heparin-binding compounds is for stent or blood vessel construction.

For the embodiments above, the PEG and the PEG molecules in each conjugate can be the same or different types of PEG. In one embodiment, the PEG-LMWH conjugates in the noncovalent crosslinkings comprise multi-arm PEG, eg. 4-arm or 8-arm star PEG. Likewise, the first LMWH and the LMWH molecules in each conjugate can be the same or different types of LMWH. In one embodiment, the LMWH molecules comprise nadroparin, dalteparin, reviparin, ardeparin, enoxaparin, tinzaparin, fondaparinux, parnaparin or certaparin. The first and second heparin-binding compounds can be the same or different types of compounds. In one embodiment, the heparin-binding compounds comprise growth factor, cytokine, peptide, peptide-modified polymer, protein, polysaccharide, polysaccharide-modified polymer, peptoid, peptoid-modified polymer or a small molecular drug. In another embodiment, the heparin-binding compounds comprise vascular endothelial growth factor, basic fibroblast growth factor, acidic fibroblast growth factor, heparin-binding epidermal growth factor, transforming growth factor-beta or nerve growth factor. In another embodiment, the heparin-binding compounds comprise a compound selected from the group consisting of F56, V1, GU40C4, K237 and QK.

Covalently crosslinked PEG and heparin hydrogel networks have been previously investigated using high molecular weight heparin to yield growth factor delivery depots in vivo and in vitro.[1,2] The use of a combination of covalent and noncovalent crosslinks, however, permit the formulation of mechanically robust, yet environmentally responsive, hydrogels, sensitive to addition of proteins or other engineered macromolecules. In some embodiments, the covalently crosslinked portion polymer of the polymer matrix s at least 1.5, at least 2.0, or at least 3.0 weight percent. In other embodiments, the polymer matrix is about 1.5 to about 3.0 weight percent covalently crosslinked.

Figure 30:
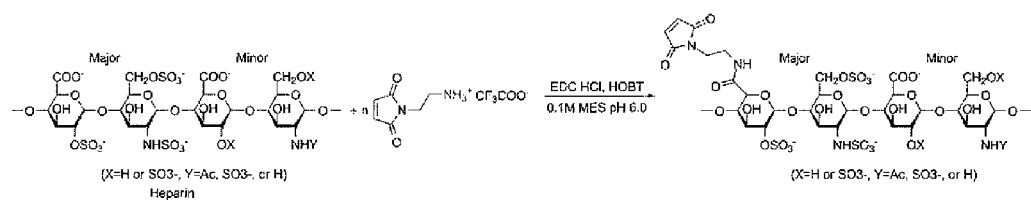
FIG. 30 shows a modification of LMWH with maleimide groups via the attachment of aminoethylmaleimide (AEM) via simple carbodiimide chemistries.

In some embodiments, crosslinking strategies have been developed employing LMWH as the heparin species in the PEG-based hydrogels. In one particular embodiment, LMWH was modified with maleimide groups via the attachment of aminoethylmaleimide (AEM) via simple carbodiimide chemistries to yield a functionality of 1.7 maleimides per LMWH chain.[1] See FIG. 30.

Figure 31:
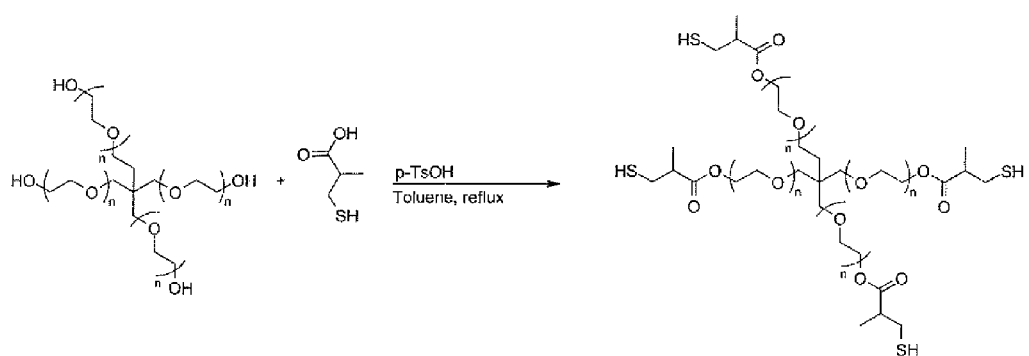
FIG. 31 shows a four-arm polyethylene glycol) mercaptoisobutanoate synthesis scheme.

In some embodiments, linear PEG may be used. In other embodiments, multi-arm PEG, e.g. four-arm PEG, four-arm star PEG, eight-arm PEG, eight-arm star PEG, may be used. Four-arm PEG provides multiple, intermolecular crosslinking sites. The PEG may be esterified with 3-mercaptoisobutyric acid to provide a neighboring methyl group to the ester to stabilize the esterified species and thus increase the degradation timescales. See FIG. 31.

Figure 32:
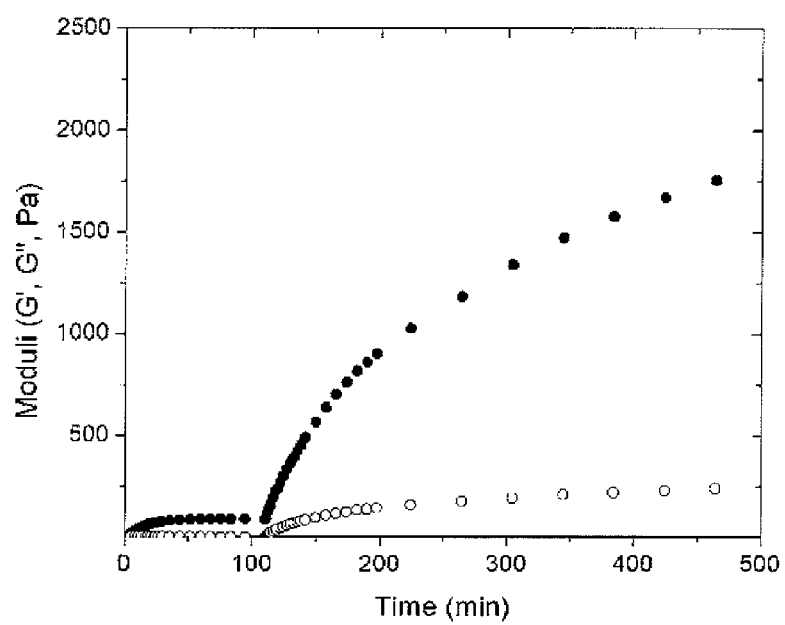
FIG. 32 shows a time sweep torsion test which shows the increase in loss modulus (G", ●) and storage modulus (G', ○) upon swelling a 2 wt % hydrogel with 5 μL 88 mg/ml lysozyme solution at 100 minutes (LMWH:Lysozyme=3:1), indicated by the starred arrow.

These chemical strategies provide a useful and simple means to produce LMWH-functionalized hydrogels of varying mechanical strength, into which additional proteins can be added, to provide additional noncovalent crosslinks that alter the mechanical properties of the gel and that are environmentally responsive. In one particular embodiment, the proteins chosen for noncovalent crosslinking may comprise lysozyme and VEGF. Lysozyme is a model protein that is used to determine the feasibility of preparing and characterizing a hydrogel crosslinked via both covalent and noncovalent interactions. Lysozyme is a 14 kDa protein with a pI of ~10.5, with a positive charge distributed over the surface of the protein.[3] Low molecular weight heparin is capable of binding 2-3 lysozymes per chain.[3] To avoid flocculation of lysozyme-heparin complexes prior to gel formation, hydrogels may be first formed with subsequent swelling with lysozyme solutions. The change in elastic modulus of these materials upon the addition of lysozyme is illustrated in FIG. 32. As shown in FIG. 32, after 100 minutes of equilibration in buffer, the hydrogel had reached equilibrium at which it was then incubated with a lysozyme solution. An immediate increase in modulus was observed. FIG. 32 shows a time sweep torsion test which shows the increase in loss modulus (G", ●) and storage modulus (G', ○) upon swelling a 2 wt % hydrogel with 5 µL 88 mg/ml lysozyme solution at 100 minutes (LMWH:Lysozyme=3:1), indicated by the starred arrow.

In one embodiment, heparin-binding growth factor, namely VEGF (vascular endothelial growth factor), is used to noncovalently crosslink four arm PEG-low molecular weight heparin macromolecules.[4] The shear modulus of these solely noncovalently crosslinked materials was approximately 1 Pa. The utility and mechanical properties of these solely noncovalently crosslinked materials can be improved by the addition of covalent crosslinking. In some embodiments, hydrogels comprising covalent and noncovalent crosslinking have an elastic modulus of at least 5 Pa or at least 10 Pa. In other embodiments, hydrogels comprising covalent and noncovalent crosslinking have a elastic modulas of about 5 Pa to about 10 Pa.

Figure 33:
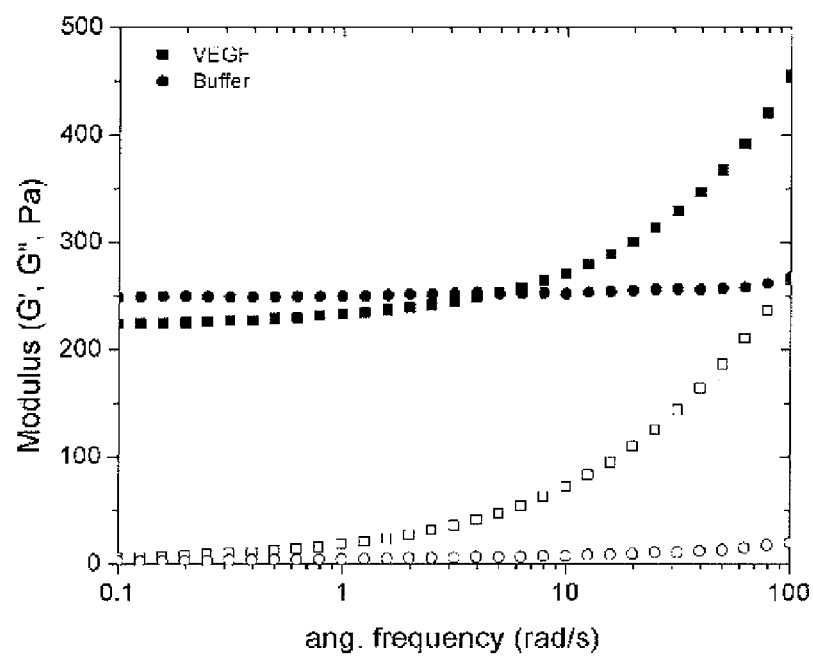
FIG. 33 shows a frequency sweep torsion test showing an increase in higher frequency mechanical properties for swelling a 3 wt % hydrogel with 200 ul 5 mg/ml VEGF solution (Hep:VEGF=33:1). Circles indicate results from swelling with buffer, squares from VEGF. Closed symbols are storage modulus (G'), open are loss modulus (G").

In FIG. 33, the feasibility to alter the mechanical properties of a covalently crosslinked PEG-LMWH gel via the addition of VEGF at low concentrations is demonstrated. FIG. 33 shows a frequency sweep torsion test showing an increase in higher frequency mechanical properties for swelling a 3 wt % hydrogel with 200 ul 5 mg/ml VEGF solution (Hep: VEGF=33:1). Circles indicate results from swelling with buffer, squares from VEGF. Closed symbols are storage modulus (G'), open are loss modulus (G"). The data in FIG. 33 show that a 3 wt % gel swelled with 200 ul of 5 mg/ml VEGF shows an increase in torsional stiffness (i.e. shear storage modulus) with increasing frequency. G" increased by 13× and G' increased by 1.7× at 100 rad/s. The responsiveness of the hydrogel is apparent at higher frequencies. Lower molecular weight heparin should form a more responsive hydrogel than higher molecular weight heparin.

In one embodiment, the use of low molecular weight heparins (e.g. Approx Mw 4,500 g/mol, ~15 saccharides) is preferred because the VEGF can engage one LMWH at each of the VEGF's heparin-binding sites to yield a functional crosslink. In some embodiments, the LMWH has a MW less than about 6,000 g/mol. In other embodiments, the LMWH has a MW of about 3,000 g/mol. The use of PEG-HMWH gels (high molecular weight heparin) displays less VEGF responsiveness. VEGF carries two heparin binding domains; each domain has been determined to bind 6-8 saccharides; thus, in the presence of high molecular weight heparin, it is possible for VEGF to bind to a single heparin chain.[5,6] Such binding does not yield a functional crosslink between PEG chains. In contrast, the use of LMWH in the network limits this intramolecular binding of VEGF with heparin, and the VEGF binds intermolecularly with two separate LMWH and thus links two separate PEG chains.

The feasibility of using this system to create responsive hydrogels has been shown. Responsive networks are also possible via interactions of covalently crosslinked PEG-LMWH with a variety of other heparin-binding molecules. The use of anti-angiogenic, heparin-binding peptides would yield therapeutic materials capable of targeted delivery to sites of pathological angiogenesis (e.g., tumors). The following Table lists peptides or peptoids that have been shown to bind to the VEGFR-2 receptor (also known as KDR), thus blocking angiogenesis. These compounds can be attached to a heparin binding peptide sequence, sHIP (CKAAKRPKAAKDKQTK) (SEQ ID NO:8) or others, and subsequently to 4-arm star PEG to yield heparin-binding, therapeutic crosslinking molecules.

| Peptide | Sequence | SEQ ID NO: | VEGF Receptor |
|---|---|---|---|
| F56[8] | WHSDMEWWYLLG | 4 | FLT-1 |
| V1[9] | ATWLPPR | 5 | KDR |
| GU40C4[10] | Peptoid | — | KDR |
| K237[11] | HTMYYHHYQHHL | 6 | KDR |
| QK[12] | KLTWQELYQLKYKGI | 7 | KDR |

In some embodiments, the hydrogels of the present invention may further comprise a second noncovalent crosslink, wherein the second noncovalent crosslink comprises a fifth and sixth PEG-LMWH conjugate, and a PEG-heparin-binding peptide conjugate wherein the PEG-heparin-binding peptide conjugate comprises two heparin-binding peptides that are covalently attached to the PEG molecule of the PEG-heparin-binding peptide conjugate, wherein the PEG molecule of each PEG-LMWH conjugate is covalently attached to the polymer matrix, wherein the LMWH molecule of each PEG-LMWH conjugate is covalently attached to the PEG molecule of the same conjugate, and wherein the LMWH molecule of each PEG-LMWH conjugate is noncovalently attached to a different heparin-binding peptide of the PEG-heparin-binding peptide conjugate. In another embodiment, the heparin-binding peptide can be PF$_4$ZIP, RRP (CGGR-RRRRRRGG) (SEQ ID NO:9), HIP, sHIP (CKAAKRPKAAKDKQTK) or ATIII. As before, the PEG and LMWH molecules may be the same as used in the hydrogel or may be different compounds.

FIGS. 34 and 35 show different crosslinks of the present invention. The present invention may comprise one or more of the crosslinks shown in the Figures. Specifically, FIG. 34 shows different crosslink embodiments of the present invention. An example of a covalent crosslink comprising PEG and LMWH is shown in A. An example of either covalent, non-covalent or a crosslink with a mixture of both covalent and non-covalent attachments is shown in B. The crosslinks in B comprise PEG, LMWH and a heparin-binding compound (HBC). An example of a noncovalent crosslink comprising PEG, LMWH and heparin-binding peptide is shown in C. In these embodiments, as well as the others disclosed herein, any branched (e.g. 4-arm star PEG, 8-arm star PEG) or non-branched PEG can be used.

FIG. 35 shows additional example of crosslinked embodiments of the present invention. An example of a covalent crosslink comprising PEG and LMWH is shown in D wherein a heparin-binding compound is attached to the PEG. Another example of a covalent crosslink comprising PEG and a heparin-binding compound wherein a LMWH is attached to the PEG.

Experimental

LMWH-AEM synthesis Low-molecular weight heparin (LMWH, $M_w$ 4,500 g/mol) was reacted with N-(2-aminoethyl) maleimide trifluoroacetate salt (AEM, 5 meq.) using standard procedures to generate LMWH-AEM. The degree of maleimide functionalization of approximately 1.7 per LMWH chain.

Four-Arm Poly(ethylene glycol) mercaptoisobutanoate (4-arm PEG MIB) synthesis Four-arm hydroxyl terminated poly(ethylene glycol) (PEG, Mn 10,000 g/mol) was reacted with mercaptoisobutyric acid (MIB) using standard procedures to generate 4arm PEG MIB.

Hydrogel Formation LMWH AEM and 4arm PEG MIB were combined to successfully form a hydrogel.

References

1. Nie, T.; Baldwin, A.; Yamaguchi, N.; Kiick, K. L. Journal of Controlled Release 2007, 122, 287-296.
2. Tae, G.; Kim, Y. J.; Choi, W. I.; Kim, M.; Stayton, P. S.; Hoffman, A. S. Biomacromolecules 2007, 8, 1979-1986.
3. Van de Weert, M.; Andersen, M. B.; Frokjaer, S. Pharmaceutical Research 2004, 21, 2354-2359.
4. Yamaguchi, N.; Zhang, L.; Chae, B. S.; Palla, C. S.; Furst, E. M.; Kiick, K. L. J Am Chem Soc 2007, 129, 3040-3041.
5. Ashikari-Rada, S.; Habuchi, H.; Kariya, Y.; Itoh, N.; Reddi, A. H.; Kimata, K. J Biol Chem 2004, 279, 12346-12354.
6. Robinson, C. J.; Mulloy, B.; Gallagher, J. T.; Stringer, S. E. J Biol Chem 2006, 281, 1731-1740.
7. Fichter, K. M.; Zhang, L.; Kiick, K. L.; Reineke, T. M. Bioconjugate Chemistry 2007, 19, 76-88.
8. An, P.; Lei, H.; Zhang, J.; Song, S.; He, L.; Jin, G.; Liu, X.; Wu, J.; Meng, L.; Liu, M.; Shou, C. International Journal of Cancer 2004, 111, 165-173.
9. Binetruy-Tournaire, R.; Demangel, C.; Malavaud, B.; Vassy, R.; Rouyre, S.; Kraemer, M.; Plouet, J.; Derbin, C.; Perret, G.; Mazie, J. C. EMBO Journal 2000, 19, 1525-1533.
10. Udugamasooriya, D. G.; Dineen, S. P.; Brekken, R. A.; Kodadek, T. Journal of the American Chemical Society 2008, 130, 5744-5752.
11. Hetian, L.; Ping, A.; Shumei, S.; Xiaoying, L.; Luowen, H.; Jian, W.; Lin, M.; Meisheng, L.; Junshan, Y.; Chengchao, S. J Biol Chem 2002, 277, 43137-43142.
12. D'Andrea, et al. PNAS USA, 2005, 102 (40), 14215-14220.

What is claimed:

1. A hydrogel comprising a matrix, the matrix comprising a cross-linking structure selected from the group consisting of
   (A) PEG-LMWH-PEG,
   (B) PEG-LMWH-HBC-LMWH-PEG,
   (C) PEG-LMWH-HBC-PEG*-HBC-LMWH-PEG,
   (D) PEG-LMWH-PEG-HBC, and
   (E) LMWH-PEG-HBC-PEG*;
wherein the hydrogel further comprises a natural or synthetic polymer; wherein the PEG in a PEG-LMWH conjugate or in a LMWH-PEG conjugate is covalently bound to the LMWH, and is covalently bound to the polymer, and is branched or unbranched; wherein the HBC is bound to the LMWH molecule by a covalent bond or a non-covalent bond, or wherein the HBC is covalently bound to the PEG molecule in the PEG-LMWH conjugate, or wherein the HBC is covalently bound to a PEG* molecule, wherein the PEG* molecule is a PEG molecule that is not covalently attached to the LMWH, and wherein the PEG* molecule is branched or unbranched.

2. The hydrogel of claim 1, wherein the matrix comprises two or more cross-linking structures selected from (A), (B), (C), (D), and (E).

3. The hydrogel of claim 2, wherein the cross-linking structures are (A) and (B).

4. The hydrogel of claim 2, wherein the cross-linking structures are (A) and (C).

5. The hydrogel of claim 1, wherein the cross-linking structure is (D).

6. The hydrogel of claim 1 wherein the portion of the matrix covalently crosslinked to the polymer is at least 1.5 weight percent.

7. The hydrogel of claim 1 having an elastic modulus of at least 5 Pa.

8. The hydrogel of claim 1 wherein the LMWH molecules are selected from the group consisting of nadroparin, dalteparin, reviparin, ardeparin, enoxaparin, tinzaparin, fondaparinux, parnaparin or certaparin.

9. The hydrogel of claim 1 wherein the heparin-binding compound (HBC) is selected from one or more of growth factors, cytokines, peptides, peptide-modified polymers, proteins, polysaccharides, polysaccharide-modified polymers, peptoids, peptoid-modified polymers and small molecule drugs.

10. The hydrogel of claim 9 wherein the heparin-binding compound (HBC) is a growth factor selected from vascular endothelial growth factor, basic fibroblast growth factor, acidic fibroblast growth factor, heparin-binding epidermal growth factor, transforming growth factor-beta and nerve growth factor.

11. The hydrogel of claim 1 wherein the heparin-binding compound (HBC) is selected from the group consisting of F56, V1, GU40C4, K237 and QK.

12. The hydrogel of claim 1 wherein the heparin-binding compound (HBC) is selected from $PF_4ZIP$, RRP, HIP, sHIP and ATIII.

* * * * *

UNITED STATES PATENT AND TRADEMARK OFFICE
CERTIFICATE OF CORRECTION

PATENT NO. : 8,367,639 B2
APPLICATION NO. : 12/814826
DATED : February 5, 2013
INVENTOR(S) : Kristi L. Kiick and Nori Yamaguchi It is certified that error appears in the above-identified patent and that said Letters Patent is hereby corrected as shown below:

Title page, item (12) and (75), the first inventor's name is misspelled on the face page of the issued patent. The name appears as "Kristi L. Kilck," but the correct name is "Kristi L. Kiick".

Signed and Sealed this
Nineteenth Day of March, 2013

Teresa Stanek Rea
*Acting Director of the United States Patent and Trademark Office*

SEQUENCE LISTING

<160> NUMBER OF SEQ ID NOS: 9

<210> SEQ ID NO 1
<211> LENGTH: 34
<212> TYPE: PRT
<213> ORGANISM: Artificial sequence
<220> FEATURE:
<223> OTHER INFORMATION: Synthetic peptide

<400> SEQUENCE: 1

Cys Gly Gly Arg Met Lys Gln Leu Glu Asp Lys Val Lys Lys Leu Leu
1               5                   10                  15

Lys Lys Asn Tyr His Leu Glu Asn Glu Val Ala Arg Leu Lys Lys Leu
            20                  25                  30

Val Gly

<210> SEQ ID NO 2
<211> LENGTH: 15
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Ala is beta-alanine

<400> SEQUENCE: 2

Cys Lys Ala Phe Ala Lys Leu Ala Ala Arg Leu Tyr Arg Lys Ala
1               5                   10                  15

<210> SEQ ID NO 3
<211> LENGTH: 16
<212> TYPE: PRT
<213> ORGANISM: Homo sapiens

<400> SEQUENCE: 3

Cys Arg Pro Lys Ala Lys Ala Lys Ala Lys Ala Lys Asp Gln Thr Lys
1               5                   10                  15

<210> SEQ ID NO 4
<211> LENGTH: 12
<212> TYPE: PRT
<213> ORGANISM: Artificial sequence
<220> FEATURE:
<223> OTHER INFORMATION: Synthetic peptide

<400> SEQUENCE: 4

Trp His Ser Asp Met Glu Trp Trp Tyr Leu Leu Gly
1               5                   10

<210> SEQ ID NO 5
<211> LENGTH: 7
<212> TYPE: PRT
<213> ORGANISM: Artificial sequence
<220> FEATURE:
<223> OTHER INFORMATION: Synthetic peptide

<400> SEQUENCE: 5

Ala Thr Trp Leu Pro Pro Arg
1               5

<210> SEQ ID NO 6
<211> LENGTH: 12
<212> TYPE: PRT
<213> ORGANISM: Artificial sequence
<220> FEATURE:

```
<223> OTHER INFORMATION: Synthetic peptide

<400> SEQUENCE: 6

His Thr Met Tyr Tyr His His Tyr Gln His His Leu
1               5                   10

<210> SEQ ID NO 7
<211> LENGTH: 15
<212> TYPE: PRT
<213> ORGANISM: Artificial sequence
<220> FEATURE:
<223> OTHER INFORMATION: Synthetic peptide

<400> SEQUENCE: 7

Lys Leu Thr Trp Gln Glu Leu Tyr Gln Leu Lys Tyr Lys Gly Ile
1               5                   10                  15

<210> SEQ ID NO 8
<211> LENGTH: 16
<212> TYPE: PRT
<213> ORGANISM: Artificial sequence
<220> FEATURE:
<223> OTHER INFORMATION: Synthetic peptide

<400> SEQUENCE: 8

Cys Lys Ala Ala Lys Arg Pro Lys Ala Ala Lys Asp Lys Gln Thr Lys
1               5                   10                  15

<210> SEQ ID NO 9
<211> LENGTH: 12
<212> TYPE: PRT
<213> ORGANISM: Artificial sequence
<220> FEATURE:
<223> OTHER INFORMATION: Synthetic peptide

<400> SEQUENCE: 9

Cys Gly Gly Arg Arg Arg Arg Arg Arg Arg Gly Gly
1               5                   10
```